United States Patent
Wendell et al.

(10) Patent No.: US 6,355,164 B1
(45) Date of Patent: Mar. 12, 2002

(54) SAMPLE COLLECTION APPARATUS AND METHOD FOR MULTIPLE CHANNEL HIGH THROUGHPUT PURIFICATION

(75) Inventors: Don Wendell, San Diego; Romaine Maiefski, Ocean Side; Jonathan D. Krakover, Visa, all of CA (US)

(73) Assignee: Ontogen Corporation, Carlsbad, CA (US)

(*) Notice: Subject to any disclaimer, the term of this patent is extended or adjusted under 35 U.S.C. 154(b) by 0 days.

(21) Appl. No.: 09/569,382

(22) Filed: May 11, 2000

Related U.S. Application Data

(63) Continuation-in-part of application No. 09/430,194, filed on Oct. 29, 1999.

(51) Int. Cl.⁷ .............................. B01D 15/08
(52) U.S. Cl. .............. 210/198.2; 210/656; 210/659; 210/143; 422/63; 422/70; 422/100
(58) Field of Search .................. 210/635, 656, 210/659, 143, 198.2; 95/82; 96/102; 422/63, 70, 101; 436/161

(56) References Cited

U.S. PATENT DOCUMENTS

| | | | |
|---|---|---|---|
| 2,733,135 A | 1/1956 | Huckabay | 23/230 |
| 3,250,395 A | 5/1966 | Blume | 210/198.2 |
| 4,079,009 A | 3/1978 | Seiler et al. | 210/198.2 |
| 4,554,071 A | 11/1985 | Ruijten et al. | 210/198.2 |
| 4,719,011 A | 1/1988 | Shalon et al. | 210/198.2 |
| 4,766,082 A * | 8/1988 | D'Autry | 210/198.2 |
| 4,787,971 A | 11/1988 | Donald | 210/198.2 |
| 5,234,599 A | 8/1993 | Cortes et al. | 210/659 |
| 5,670,054 A | 9/1997 | Kibbey et al. | 210/659 |
| 5,938,932 A | 8/1999 | Connelly et al. | 210/659 |
| 6,080,318 A * | 1/2000 | Gumm | 210/659 |
| 6,054,047 A * | 4/2000 | Hindsgaul | 210/198.2 |
| 6,090,280 A * | 7/2000 | Connelly | 210/198.2 |
| 6,197,198 B1 * | 3/2001 | Messnger | 210/656 |
| 6,210,571 B1 * | 4/2001 | Zambias | 210/198.2 |

FOREIGN PATENT DOCUMENTS

| | | | |
|---|---|---|---|
| SU | 940057 | 6/1982 | 210/198.2 |
| WO | WO 98/35227 | 8/1998 | 210/198.2 |

OTHER PUBLICATIONS

E. Von Arx, P. Richert, R. Stoll, K. Wagner, and Wuest, "New Aids for Preparative High–Performance Liquid Chromatography", Journal of Chromatography, 1982, vol. 238, 419–425.

Michael J. Kessler, "Quantitation of Radiolabeled Biological Molecules Separated by High–Performance Liquid Chromatography", Journal of Chromatography, 1983, vol. 255, pp. 209–217.

(List continued on next page.)

*Primary Examiner*—Ernest G. Therkorn
(74) *Attorney, Agent, or Firm*—Perkins Coie, LLP

(57) ABSTRACT

A fraction collection assembly having a frame and a dispensing head movably connected to the frame for movement about three axes. The dispensing head has a dispensing tube that receives and dispenses the sample portion. The dispensing head is movable between a dispensing position, a rinse position, and a pickup position. A receiving container with a receiving well is positioned to receive the sample portion of the selected sample dispensed from the dispensing tube when the dispensing head is in the dispensing position. The receiving well has a 1-to-1 corresponding position to the well from which the sample is originally taken from the supplying container. The rinse station is connected to the frame and positioned to removably receive the dispensing tube when the dispensing head is in the rinse position. A pickup station is provided adjacent to an expansion chamber distribution assembly to retain the expansion chambers in a selected position to be picked up by the dispensing head when in the pick up position prior to distribution of the sample into the receiving container.

33 Claims, 30 Drawing Sheets

OTHER PUBLICATIONS

Robert M. Campbell and Milton L. Lee, "Supercritical Fluid Fractionation of Petroleum– and Coal–Derived Mixtures", Anal. Chem., 1986, vol. 58, No. 11, pp. 2247–2251.

Johan Uusijarvi, Borje Egestad, and Jan Sjovall, "Manual and Automated Enrichment Procedures for Biological Samples using Lipophilic Gels", Journal of Chromatography, 1989, vol. 488, pp. 87–104.

Tooru Imahashi, Yoshio Yamauchi, and Munco Saito, "Fractionation and Identification of Additives in Polyvinylchloride Film by Supercritical Fluid Extraction/Semi–Preparative Supercritical Fluid Chromatography", Bunseki Kagaku, 1990, vol. 39, pp. 79–85.

Hans M.H. van Eijk, Mark P.L. Huinck, Dennis R. Rooyakkers, and Nicolaas E.P. Deutz, "Automated Simultaneous Isolation and Quantitation of Labeled Amino Acid Fractions From Plasma and Tissue by Ion–Exchange Chromatography", Journal of Chromatography B, 1994, vol. 660, pp. 251–257.

John F. Cargill and Romaine R. Maiefski, "Automated Combinatorial Chemistry on Solid Phase", Laboratory Robotics and Automation, 1996, vol. 8, pp. 139–148.

Robert Pal, Kristina Tolvaj, and Miklos Juhasz, "Separation of Gas Oil Samples by Coupled Packed and Open Tubular Column SFC", J. Microcolumn Separations, 1996, vol. 8, pp. 269–273.

Bradley L. Ackermann and Brian T. Regg, "Rapid Analysis of Antibiotic–Containing Mixtures From Fermentation Broths by Using Liquid Chromatography–Electrospray Ionization–Mass Spectrometry and Matrix–Assisted Laser Desporption Ionization–Time–of–Flight–Mass Spectrometry", Journal of the American Society of Mass Spectrometry, 1996, vol. 7, pp. 1227–1237.

Donald J. Daley, Russel D. Scammell, David James, Iain Monks, Roberto Raso, Alison E. Ashcroft, and Aaron J. Hudson, "High–Throughput LC–MS Verification of Drug Candidates From 96–Well Plates", Am. Biotechnol. Lab., Nov. 1997, vol. 15, pp. 24, 26, and 28.

Christopher E. Kibbey, "An Automated System for the Purification of Combinatorial Libraries by Preparative LC/MS", Laboratory Robotics and Automation, 1997, vol. 9, pp. 309–321.

L. Zeng, L. Burton, K. Yung, B. Shushan, and D.B. Kassel, "Automated Analytical/Preparative High–Performance Liquid Chromatography–Mass Spectrometry System for the Rapid Characterization and Purification of Compound Libaries", Journal of Chromatography A, Jan. 23, 1998, vol. 794, Nos. 1 and 2, pp. 3–13.

Chemical Abstracts, vol. 128, No. 13, Mar. 30, 1998, Angelika Weber, Holger Theils, and Reza Hashemi, "Automated and Flexible Chromatographic Purification, Part 2. Experiences in the Operational Phase", p. 1320, Col. 2, Abstract No. 162374p, LaborPraxis, 1998, 22(1), 43–44.

Chemical Abstracts, vol. 129, No. 7, Aug. 17, 1998, Jeffrey Kiplinger et al., "Structure–Controlled Automated Purification of Parallel Synthesis Products in Drug Discovery", p. 655, Col. 2, Abstract No. 81293e, Rapic Commun. Mass Spectrom., 1998, 12(10), 658–664.

T. Wang, L. Zeng, T. Strader, L. Burton, and Daniel B. Kassel, "A New Ultra–High Throughput Method for Characterizing Combinatorial Libraries Incorporating a Multiple Probe Autosampler Coupled with Flow Injection Mass Spectrometry Analysis", Rapid Commun. Mass Spectrom., 1998, vol. 12, pp. 1123–1129.

Lu Zeng and Daniel B. Kassel, "Developments of a Fully Automated Parallel HPCL/Mass Spectrometry System for the Analytical Characterization and Preparative Purification of Combinatorial Libraries", Anal. Chem., 1998, vol. 70, pp. 4380–4388.

F. Vérillon, D. Heems, B. Pichon, K. Coleman, and J.–C. Robert, "Supercritical fluid chromatography With Independent Programming of Mobile–Phase Pressure, Composition, and Flow Rate", American Laboratory, Jun. 1992, 8 pages.

M. Ashraf–Khorassani, M.B. Gandee, M.T. Combs, and L. T. Taylor, "Semipreparative Separation and Fractionation of Sulfonamides via Supercritical Fluid Chromatography", Journal of Chromatographic Science, vol. 35, Dec. 1997, pp. 593–597.

"Gilson Supercritical Fluid Chromatography", booklet reproducing chapter entitled "Analytical and Preparative Carbon Dioxide Chromatography with Automated Pressure Control and Different Detectors" by Francis Vérillon and Keith Coleman, from the Marcel Dekker, Inc. book entitled "Supercritical Fluid Chromatography with Packed Columns: Techniques and Applications", edited by Klaus Anton and Claire Berger, France, Reference 800347A, May 1998, pp. 1–49.

* cited by examiner

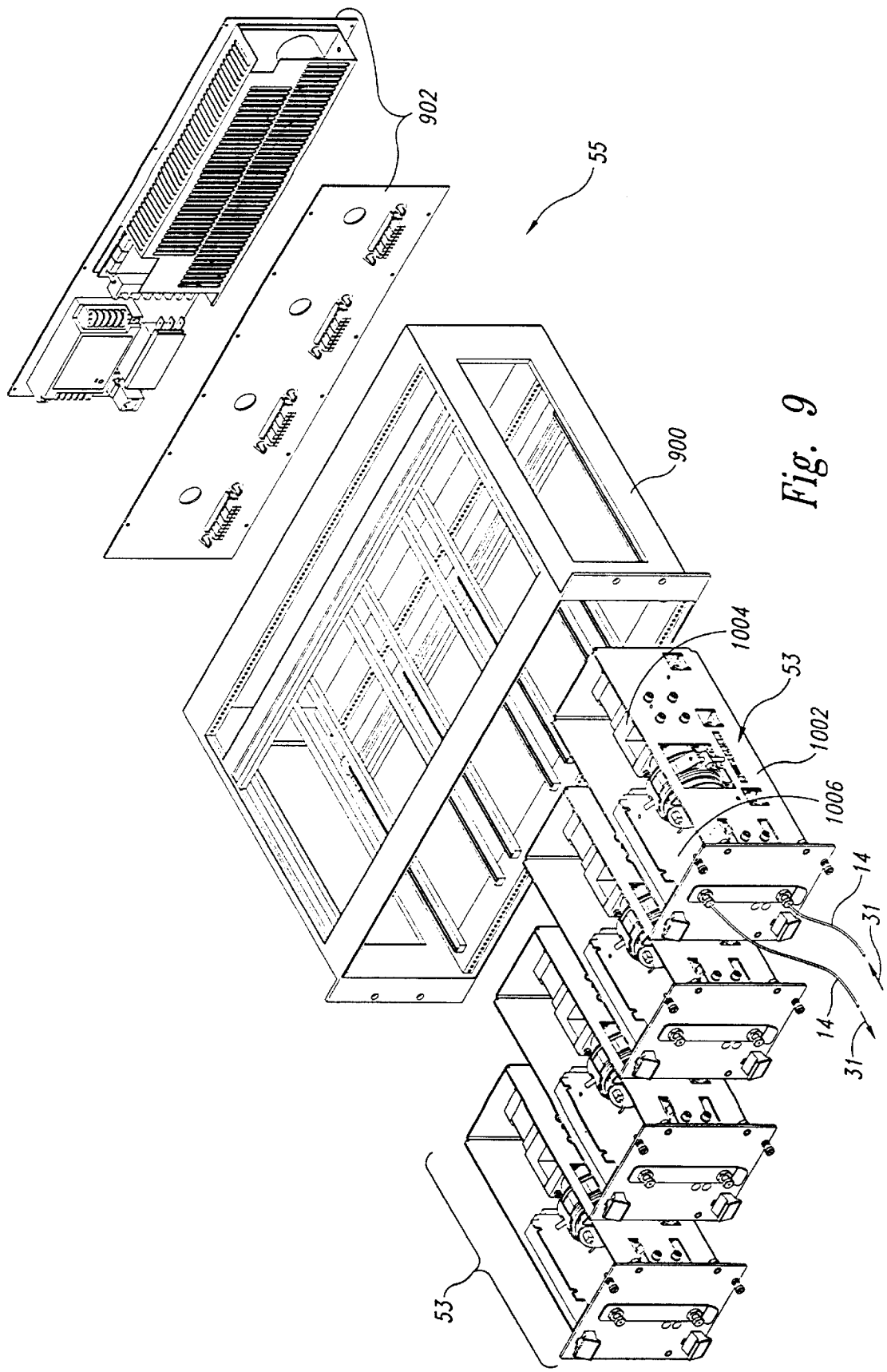

PLATE A
SAMPLE

PLATE B
TARGET

PLATE C
REACTION BY-PRODUCT

FIGURE 25

SAMPLE COLLECTION APPARATUS AND METHOD FOR MULTIPLE CHANNEL HIGH THROUGHPUT PURIFICATION

CROSS-REFERENCE TO RELATED APPLICATIONS

This application is a continuation-in-part from U.S. patent application Ser. No. 09/430,194, entitled Apparatus and Method for Multiple Channel High Throughput Purification, filed Oct. 29, 1999.

TECHNICAL FIELD

The present invention is directed to apparatus and methods for use with, as an example, sample purification, and more particularly, to collection apparatus and methods for use with, as an example, high throughput purification of samples from a chemical library.

BACKGROUND OF THE INVENTION

The relationship between structure and functions of molecules is a fundamental issue in the study of biological and other chemistry-based systems. Structure-function relationships are important in understanding, for example, the function of enzymes, cellular communication, cellular control and feedback mechanisms. Certain macromolecules are known to interact and bind to other molecules having a specific 3-dimensional spatial and electronic distribution. Any macromolecule having such specificity can be considered a receptor, whether the macromolecule is an enzyme, a protein, a glycoprotein, and antibody, or an oligonucleotide sequence of DNA, RNA, or the like. The various molecules which bind to receptors are known as ligands.

A common way to generate ligands is to synthesize molecules in a stepwise fashion in a liquid phase or on solid phase resins. Since the introduction of liquid phase and solid phase synthesis methods for peptides, oglionucleotides, and small organic molecules, new methods of employing liquid or solid phase strategies have been developed that are capable of generating thousands, and in some cases even millions of individual compounds using automated or manual techniques. A collection of compounds is generally referred to as a chemical library. In the pharmaceutical industry, chemical libraries of compounds are typically formatted into 96-well microtiter plates. This 96-well formatting has essentially become a standard and it allows for convenient methods for screening these compounds to identify novel ligands for biological receptors.

Recently developed synthesis techniques are capable of generating large chemical libraries in a relatively short period of time as compared to previous synthesis techniques. As an example, automated synthesis techniques for sample generation allows for the generation of up to 4,000 compounds per week. The samples, which contain the compounds, however, typically include 20%–60% impurities in addition to the desired compound. When samples having these impurities are screened against selected targets, such as a novel ligand or biological receptors, the impurities can produce erroneous screening results. As a result, samples that receive a positive result from initial screening must be further analyzed and screened to verify the accuracy of the initial screening result. This verification process requires that additional samples be available. The verification process also increases the cost and time required to accurately verify that the targeted compound has been located.

Samples can be purified in an effort to achieve an 85% purity or better. Screening of the purified samples provides more accurate and meaningful biological results. Conventional purification techniques, however, are very slow and expensive. As an example, conventional purification techniques using high-pressure liquid chromatography (HPLC) take approximately 30 minutes to purify each sample. Therefore, purification of the 4,000 samples generated in one week would take at least 2000 hours (i.e., 83.3 days or 2.77 months).

Conventional purification techniques, such as HPLC, also require large volumes of solvents and result in large volumes of waste solvent. Disposal of the solvents, particularly halogenated solvents, must be carefully controlled for legal and environmental reasons, so the disposal process can be laborious and very costly. Disposal of non-halogenated solvents is less rigorous. Accordingly, when halogenated and non-halogenated solvents are used, the waste solvents are separated. The separation process of large volumes of solvents, however, can be a difficult process to perform efficiently and inexpensively. Accordingly, purification of large chemical libraries can be economically prohibitive. Therefore, there is a need for a faster and more economical manner of purifying samples of large chemical libraries.

Supercritical fluid chromatography (SFC) provides faster purification techniques than HPLC. SFC utilizes a multiphase flow stream that includes a gas, such as carbon dioxide, in a supercritical state, a carrier solvent and a selected sample. The flow stream passes through a chromatography column, and is then analyzed in an effort to locate target compounds. SFC is beneficial because the solvent and sample are carried by the gas and the amount of solvent needed during a purification run is substantially less than the volume used in HPLC. Also, the amount of waste solvent at the end of a run is substantially less, so less waste solvent needs to be handled. SFC, however, requires pressure and temperature regulation that is difficult to control accurately and reliably long term.

There are many different configurations of the purification instruments. They typically share commonality in the concept wherein that samples are delivered to a chromatography instrument where compounds are separated in time, and a fraction collector collects the target compound. In order for these instruments to maintain the high throughput process, the instruments must be able to handle large sample numbers, as well as large samples in terms of mass weight and solvent volume. Tradition would specify the use of a semiprep or prep scale chromatography system for a typical milligram synthesis. While this is achievable, it has a low feasibility in a high throughput environment because several issues become apparent in such practice: large solvent usage, generation of large amounts of solvent waste, expensive large-bore columns, and relatively large collection volumes of target compounds. If the proper flow rate or column size is not used, sufficient chromatographic purity will not be achieved.

Further drawbacks experienced with high throughput purification techniques include durability of components to accommodate the high pressures, high volumes, or high flow rates of samples through the purification system. The purification system requires extreme accuracy and very high tolerances to avoid cross-contamination and to ensure purified compounds. The system components, thus, must be sufficiently durable to accept the aggressive environment while still providing the accurate results required. If the components are not sufficiently durable and they break or require repair too quickly, the purification system must be taken out of service to replace or repair the components.

A further drawback experienced in conventional purification processes of large chemical libraries includes sample management during the purification process. As an example, the chemical libraries are typically maintained in sets of 96-well microtiter plates, wherein each well includes a separate sample. Each sample is carefully tracked by its "wells address" within the microtiter plate. When a sample or portion of a sample is removed for purification from a selected well of a microtiter plate, the purified sample is typically collected in a separate container, processed, and eventually returned to a receiving well in a similar microtiter plate. That receiving well preferably has a corresponding well address in the microtiter plate so as to maintain the accuracy of the library records regarding sample location in the respective microtiter plate.

Conventional purification processes typically require the reformatting of a purified sample because the large collected volumes of fluid (e.g. the solvent that contains the purified sample) is greater than the volume of a receiving well in a conventional microtiter plate. The large collected volumes must be reduced to a volume that fits into the microtiter plate's well. The reduced volume of fluid containing the purified sample is also tracked and deposited into the appropriate well of the receiving microtiter plate that correctly maps to the well location from which the sample was taken at the start of the purification run. Such reformatting of purified samples into the receiving microtiter plate increases the time requirements and cost of the purification processes. Therefore, there is a need for a purification process that allows for quick and economical purification of samples that result in purified samples being collected directly to microtiter plates mapped directly to the original plate.

SUMMARY OF THE INVENTION

The present invention is directed to sample collection apparatus and methods for use with, as an example, multiple channel high throughput purification of samples from a chemical library that overcome drawbacks experienced in the prior art. In an illustrated embodiment of the present invention, the process of multiple channel high throughput purification simultaneously purifies a plurality of samples, such as four samples, from a chemical library.

The process includes simultaneously purifying by supercritical fluid chromatography (SFC) all four samples in four channels of a purification system. The process also includes passing a first sample along a SFC flow path of the first channel, separating the first sample into sample portions, spacing the sample portions apart from each other along at least a portion of the first fluid path. The pressure of the supercritical fluid in the flow stream is regulated with a backpressure regulator and a pressure relief valve. The method also includes moving the separated sample portions along the fluid path, and detecting at least one sample portion flowing along the fluid path. The method further includes diverting a sampling away from the sample portion, directing the sampling to an analyzer while the remainder of the sample portion continues along the fluid path.

The sampling is analyzed with the analyzer, which determines if the one sample portion has selected sample characteristics. The method also includes collecting the one sample portion in a first receptacle, such as a well of a first microtiter plate, only if the sample portion has the selected sample characteristics. If the sample portion does not have the selected sample characteristics, the sample portion is collected in a second receptacle, such as a corresponding well in a second microtiter plate.

The multiple channel high throughput purification process of this illustrated embodiment further includes purifying a second sample along a second channel substantially, simultaneously with the purification of the first sample. Purifying the second sample includes passing the second sample along a second flow path of the second channel, separating the second sample into sample portions, and spacing the sample portions apart from each other along at least a portion of the second fluid path. The method also includes moving the separated sample portions along the second fluid path, and detecting at least one of the sample portions flowing along the second fluid path. The method includes regulating the second sample's pressure along the flow path. The method further includes taking a sampling from the one sample portion and directing the sampling to the same analyzer used for the first channel. The remainder of the sample portion continues to flow along the second fluid path.

The method also includes analyzing the second sampling with the analyzer, wherein the first and second samplings are analyzed separately in accordance with a selected analysis priority protocol. The analysis of the second sampling determines if the sample portion has selected sample characteristics. The method further includes collecting the sample portion in a separate receptacle, such as a separate well in the first microtiter plate identified above, only if the sample portion has the second selected sample characteristics. If the sample portion does not have the selected sample characteristics, the sample portion is collected in another receptacle, such as a separate well in second microtiter plate identified above.

In one embodiment of the system, the method of high throughput purification includes purifying third and fourth samples along corresponding third and fourth channels in a manner similar to the purification discussed above regarding the first and second samples. In this embodiment, the same analyzer is used to analyze samplings from all four samples. The samplings are all analyzed separately and in accordance with the selected analysis priority protocol.

The system is also directed to a multiple channel high throughput purification system for substantially simultaneously purifying a plurality of samples from a chemical library. In one illustrated embodiment, the system includes a controller and a sample analyzer coupled to the controller, wherein the analyzer is configured to determine whether the samplings have selected sample characteristics. First, second, third, and fourth purification channels are coupled to the sample analyzer. The first purification channel includes a separation device positioned to receive a sample flow and to separate a first sample into sample portions so the sample portions are spaced apart from each other in the sample flow. A detector is positioned to receive the sample flow from the separation device and to detect at least one sample portion within the first sample. An adjustable backpressure regulator receives the flow stream from the detector and controls the pressure of the flow stream within the first channel.

A microsampling device is positioned to receive the sample flow from the backpressure regulator and is movable between open and closed positions while allowing a substantially continuous flow stream to pass through the device. In the closed position, the microsampling device blocks the flow stream from passing to the analyzer and allows the flow stream continues to flow through the device. In the closed position, the microsampling device also allows a substantially continuous flow of carrier fluid to pass therethrough to the analyzer. In the open position, the microsampling device directs a sampling of at least the one sample portion to the analyzer for analysis, while a remainder of the one sample portion in the sample flow moves substantially uninterrupted through the microsampling device.

A pressure relief valve receives the remainder sample flow from the microsampling device and maintains a selected pressure in the sample flow downstream of the microsampling device. A flow directing valve is in fluid communication with the first flow path and is positioned to receive the sample flow downstream of the pressure relief valves. The flow directing valve is moveable to a first position to direct the one sample portion in one direction if the analyzer has determined that the one sample portion has the selected sample characteristics. The flow directing valve is movable to a second position to direct the one sample portion in another direction if the analyzer has determined that the one sample portion does not have the selected sample characteristics. A first receptacle, such as a well of a microtiter plate, is positioned to receive the one sample portion from the flow directing device when the flow directing device is in the first position because the sample portion has the selected characteristics. A second receptacle, such as a well in a second microtiter plate, is positioned to receive the one sample portion when the flow directing device is in the second position because the sample portion does not have the selected characteristics.

The second purification channel of the purification system includes a separation device positioned to receive a second sample flow and to separate a second sample into sample portions. A separate detector is coupled to the separation device and is positioned to receive the second sample from the separation device. The detector is configured to detect at least one of the sample portions within the sample flow. A microsampling device is positioned to receive the sample flow from the detector and is movable between open and closed positions. When the microsampling device is in the closed position, the microsampling device allows the second sample flow to pass therethrough and blocks the flow from passing to the analyzer. In the open position, the microsampling device directs a sampling of the one sample portion to the analyzer for analysis, while the remainder of the sample portion continues along the second flow path substantially uninterrupted.

A back pressure regulator and a pressure relief valve receive the second sample flow upstream and downstream, respectively, of the microsampling device to selectively control the pressure of the second sample flow along the second purification channel. A flow directing valve is in fluid communication with the second flow path and is positioned to receive the sample flow therethrough. The flow directing valve is moveable to a first position to direct the one sample portion in one direction if the analyzer has determined the sample portion has the selected sample characteristic. The flow directing valve is moveable to a second position to direct the one sample portion in another direction if the analyzer has determined that the sample portion does not have the selected sample characteristics. A waste receptacle receives the remainder of the flow that does not include the sample portion.

A receptacle, such as a separate well in the first microtiter plate, is positioned to receive the sample portion from the flow directing device when the flow directing device is in the first position because the sample portion has the selected characteristics. Another receptacle, such as a separate well in the second microtiter plate, is positioned to receive the sample portion when the flow directing device is in the second position because the sample portion does not have the selected characteristics.

In one embodiment of the system, the purification system includes third and fourth purification channels that purify third and fourth samples substantially simultaneous with the purification of the first and second samples. Each of the third and fourth purification channels are coupled to the same analyzer and direct the sample portions to receptacles, such as wells in the first and second microtiter plates, discussed above.

A microsample or flow splitter valve is provided in the high throughput purification system for purifying a selected sample from a chemical library. The purification system has a sample flow path, a carrier fluid flow path, and a sample analyzer in fluid communication with the sample and carrier flow paths. The microsample valve includes a valve body having an interior chamber therein, and sample flow inlet and outlet ports in fluid communication with the sample flow path and with the interior chamber. The valve body has a carrier fluid flow port in fluid communication with the carrier fluid flow path, and an outflow port channel in fluid communication with the analyzer. A stem is slidably disposed in the interior chamber and is moveable between first and second positions within the chamber. The stem has a fluid bypass channel that communicates with the sample inlet port and the outflow port when in the first position to allow a selected portion of the sample to flow to the analyzer. The stem blocks the carrier flow port when in the first position to prevent fluid from the carrier fluid flow path from moving into the outflow port.

The fluid bypass channel in the stem communicates with the carrier flow port and with the outflow port when in the second position to allow selected carrier fluid to flow through the valve body to the analyzer. The stem blocks the sample flow inlet port from communicating with the outflow port when in the second position to prevent the sample flow from flowing to the outflow channel.

An aspect of the invention includes an automated action collection assembly that retains the microtiter plates in a fixed position and dispenses the sample portions into the selected wells in the microtiter plates. The fraction collection assembly includes a dispensing needle through which the sample portion is dispensed into disposable expansion chambers and then into the microtiter plate. The dispensing needle is mounted on a dispensing head adapted to extend into a disposable expansion chamber into which the sample portion is condensed and then dispensed into the microtiter plate.

The dispensing head is movable from a pickup station, where the expansion chambers are picked up. The expansion chambers are delivered to the pickup station from a dispenser assembly. The dispensing head picks up the expansion chambers and moves to a collection position over the microtiter plates, where the sample portions are dispensed into the selected well of the microtiter plate. The dispensing head is also movable from the dispensing position to a chamber drop-off position, where the expansion chambers are released into a waste receptacle, so the dispensing needles are exposed. The dispensing head is further movable to a wash position at a wash station on the fraction collection assembly, where the dispensing needles are washed to avoid cross-contamination between samples.

In one aspect of the invention, the automated fraction collector assembly includes a dispensing head movable relative to a frame along three axes of movement. The dispensing head is adapted to deposit the portion of the selected sample in a receiving well of a receiving container, wherein the receiving well has a one-to-one corresponding location relative to the supply well from which the sample was taken.

One embodiment includes a chambered delivery assembly sized to contain a plurality of expansion chambers and that has a delivery member positioned to deliver the expansion chambers to the pickup station. The chamber delivery system has a chamber storage portion with a plurality of the expansion chambers therein. A dispensing drum is rotatably mounted adjacent to the chamber storage portion and positioned to receive expansion chambers from the chamber storage portion. An engagement member is movably positioned adjacent to the drum to engage the expansion chamber on the dispensing drum to direct the expansion chamber to the pickup station. The fraction collection assembly of an embodiment also includes a rinse station that provides a "fluid squeegee" rinsing process for rinsing the dispensing needles of the dispensing head.

BRIEF DESCRIPTION OF THE DRAWINGS

FIG. 9 is an enlarged exploded isometric view of a back pressure regulator assembly from the purification system of FIG. 3.

FIG. 25 is a schematic view of a supplying microtiter plate with wells for containing unpurified samples and two receiving microtiter plates for a target and reaction by-products that receive purified portions of the sample in a well-to-well mapping process.

FIG. 28 is an enlarged cross-sectional view taken substantially along lines 28—28 of FIG. 26 showing a rinse station of the fraction collection assembly.

DETAILED DESCRIPTION OF THE INVENTION

The structure and function of exemplary embodiments of the present invention can best be understood by reference to the drawings. The same reference numbers may appear in multiple figures. The reference numbers refer to the same or corresponding structure in those figures.

Figure 1:
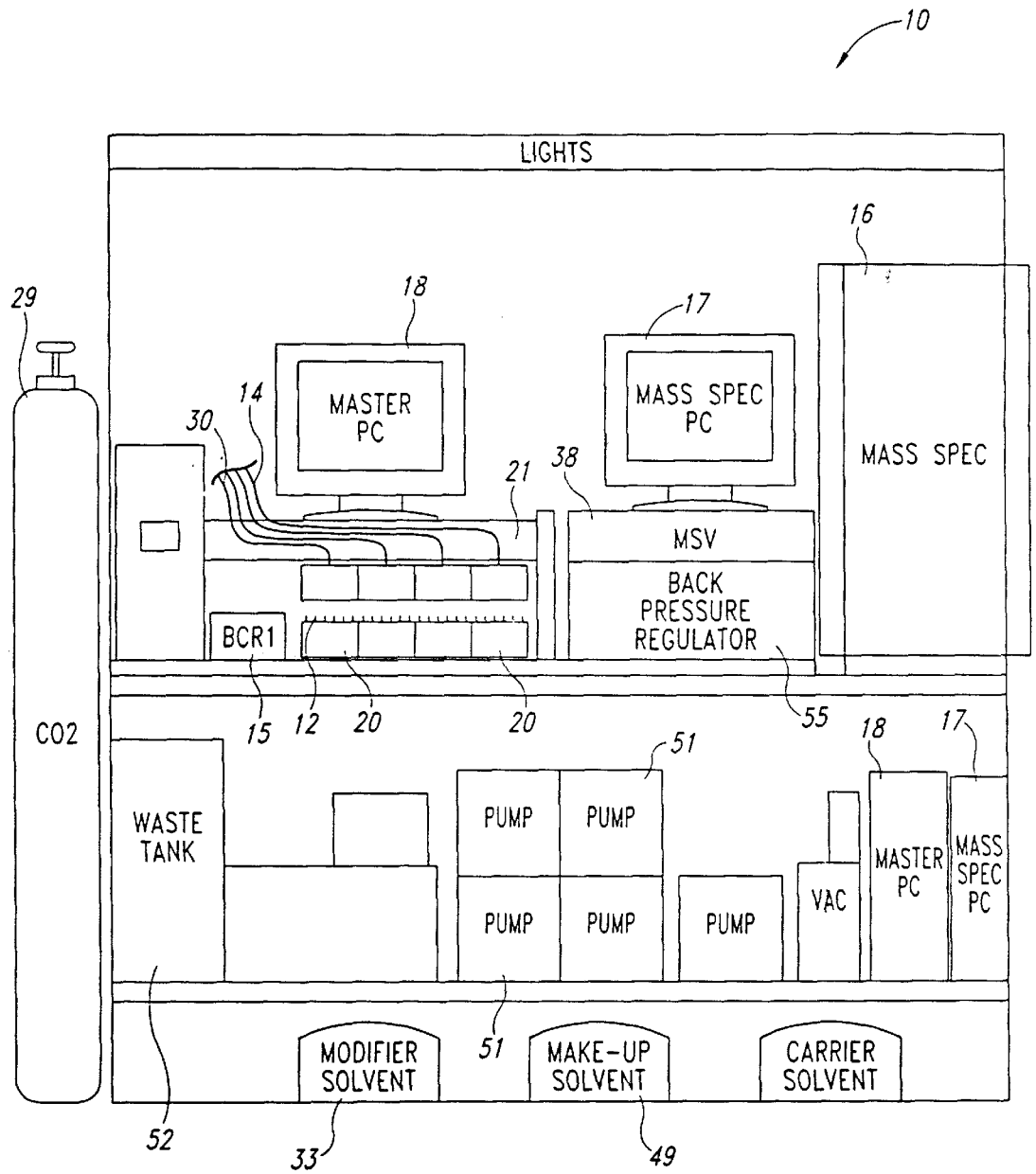
FIG. 1 is a schematic view of one portion of a multiple channel high throughput purification system having a fraction collection assembly in accordance with an embodiment of the present invention.
Figure 2:
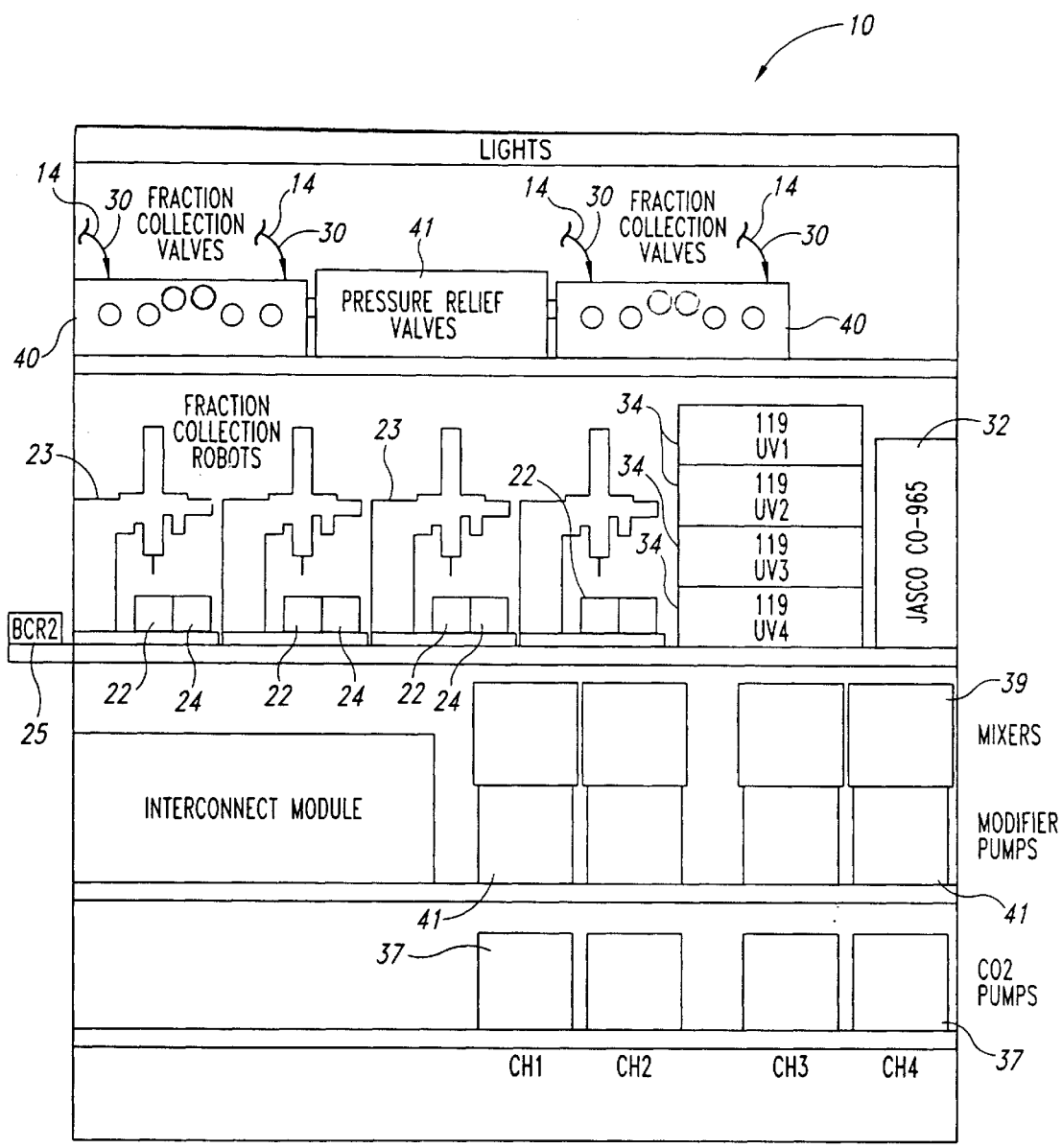
FIG. 2 is a schematic view of another portion of the multiple channel high throughput purification system of FIG. 1.
Figure 3A:
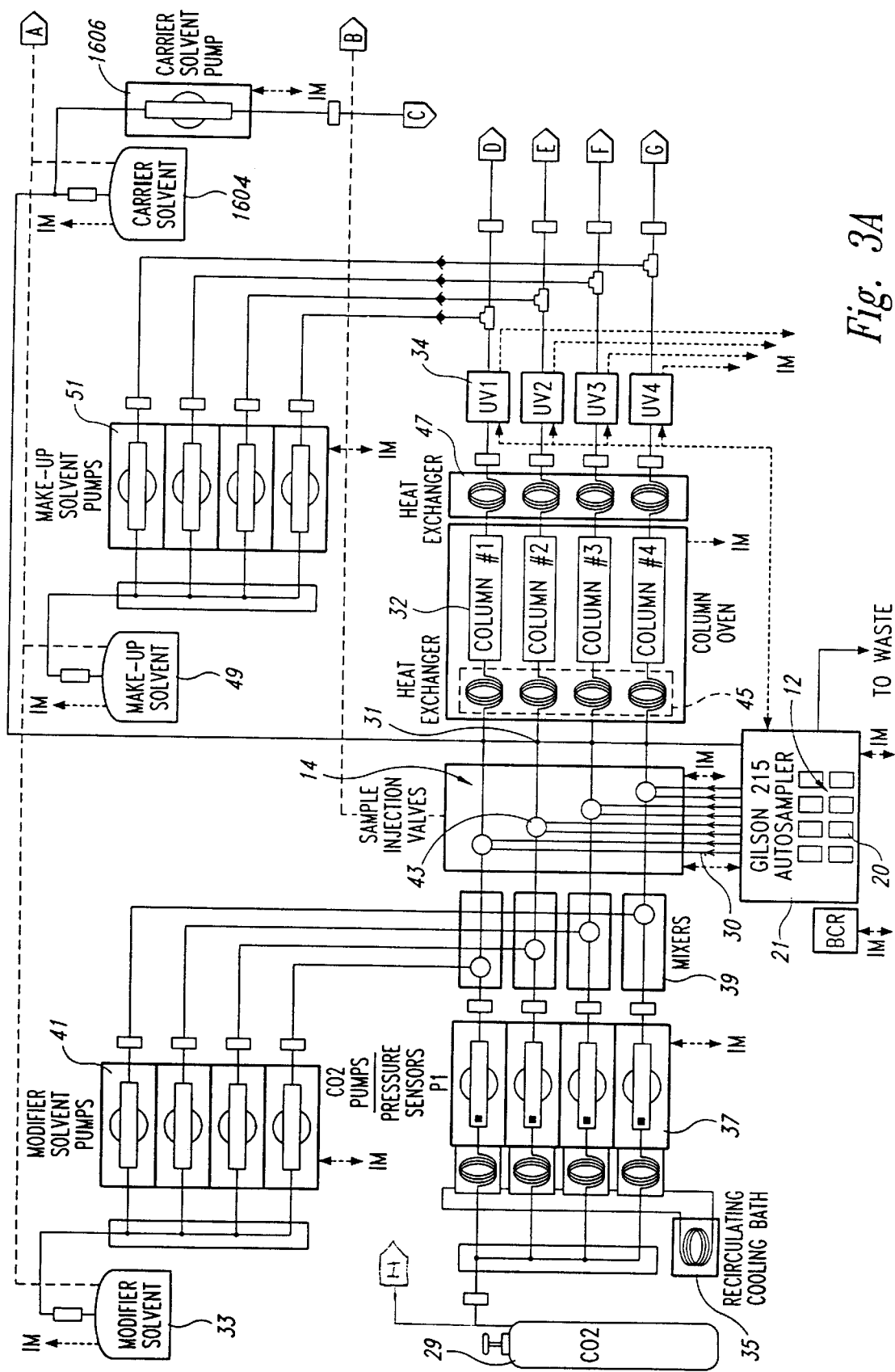
FIGS. 3A and 3B are schematic views of the multiple channel high throughput purification system of FIGS. 1 and 2, wherein the system has four channels.
Figure 3B:
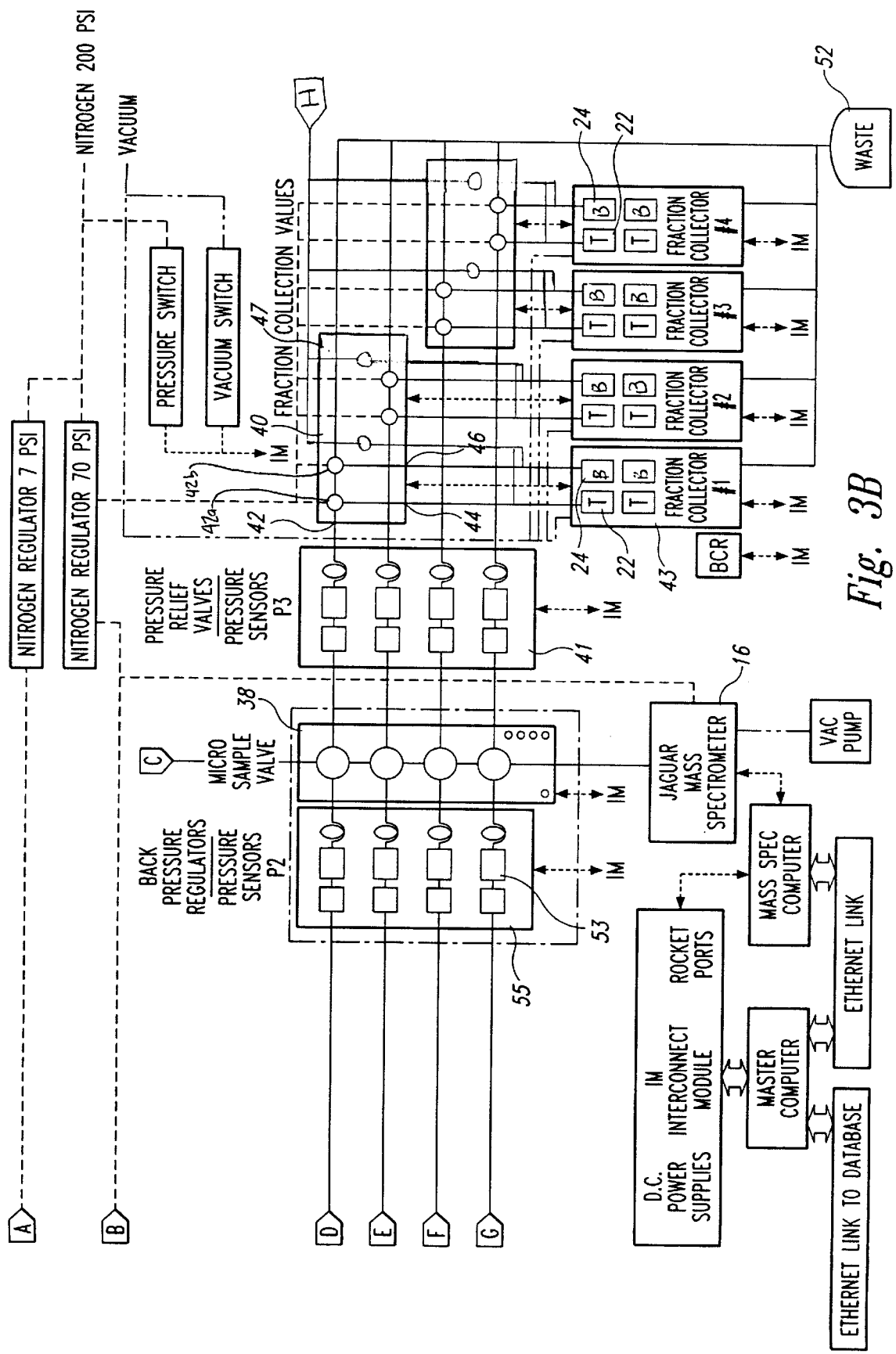

A multiple channel high throughput purification system 10 having an automated fraction collection assembly 43 in accordance with an illustrated embodiment is shown in FIGS. 1–3, and components of the system are shown in FIGS. 4–28. The illustrated purification system 10 is configured to simultaneously purify four samples 12 from a chemical library, wherein each sample is purified along a respective purification channel 14 in the system. Purification in the illustrated embodiment is achieved by chromatography, and more particularly by super critical fluid chromatography (SFC), discussed in greater detail below.

Each channel 14 receives a selected sample from a supplying microtiter plate 20. Each channel 14 is coupled to a common analyzer, such as a mass spectrometer 16 that analyzes selected portions of the samples in accordance with a predetermined analysis priority protocol. In one embodiment, the analyzer includes a plurality of compound identification devices. In the illustrated embodiment, each supplying microtiter plate 20 includes a bar code or other selected symbology or tracking mechanism that provides information specific to that supplying microtiter plate. The purification system 10 includes a bar code reader 15 or the like that identifies the specific supplying microtiter plates 20 used for each purification run.

The components of each channel 14, including the mass spectrometer 16 and the bar code reader 15, are coupled to a computer controller 18 that monitors and controls operation of the components during a purification run. The mass spectrometer 16 is also connected to a computer 17 that can provide a user with additional control or monitoring capabilities during a purification run.

After each sample 12 is analyzed by the mass spectrometer 16, a substantially purified sample portion is distributed directly into a corresponding well of a receiving microtiter plate 22 (FIG. 2) or another selected sample collector. The other portions of the sample detected by the detector, know as reaction by-products, are distributed directly into a corresponding well in a second microtiter plate 24, also illustrated in FIG. 2. Accordingly, the four samples 12 are drawn from the supplying microtiter plate 20, purified, and each sample is deposited directly into a corresponding well location in two receiving microtiter plates 22 and 24, one containing the purified target compound and the other containing the reaction by-products. In one embodiment, the four samples are drawn from the supplying microtiter plate sequentially by the same drawing needle assembly. In an alternate embodiment, the four samples are drawn substantially simultaneously by a drawing assembly having four drawing needles.

The receiving microtiter plates 22 and 24 have bar codes or the like on them, and a bar code reader 25 (FIG. 2) is provided adjacent to the receiving microtiter plates. The second bar code reader 25 is also coupled to the computer controller 18 (FIG. 1) to identify and track the samples deposited into the selected wells of each microtiter plate. The purified target compounds in the microtiter plates 22 and 24 can then be screened in a selected manner in an effort to locate a specific target compound.

The microtiter plates 22 are securely retained in an automated fraction collection assembly 23 coupled to the computer controller 18 (FIG. 1). The fraction collection assembly 23 directs selected sample portions of either purified target components or purified reaction by-products to selected wells of the microtiter plates 22 or 24. The fraction collection assembly 23 is automated and configured to pick up, clean, disposable or reusable expansion chambers in which vaporous sample portions are condensed and then delivered to the microtiter plates 22 or 24. The fraction collection assembly 23 includes a rinse station in which sample dispensing needles are rinsed after a sample portion is delivered to the respective microtiter plate and before the next set of clean expansion chambers are picked up for delivery of the next sample portions.

In the purification process of the illustrated embodiment, selected supplying microtiter plates 20 are identified by the bar code reader 15 and positioned on an autosampler 21 (FIG. 1). In one embodiment, the autosampler 21 is a Gilson 215 autosampler, manufactured by Gilson, Inc. of Middleton, Wis. As best seen in the schematic diagram of FIG. 3, each sample is drawn by the autosampler 21 from a selected well of a supplying microtitor plate 20 and is fed into a sample flow path 30 of a respective one of the four channels 14. The four samples 12 are substantially simultaneously introduced into the respective purification channels 14. Although the illustrated embodiment substantially simultaneously purifies four samples 12, other numbers of samples can be simultaneously purified with a system in accordance with the present invention.

As best seen in FIG. 3, the sample 12 is combined with carbon dioxide from a $CO_2$ source 29 and a modifier solvent from a solvent source 33 to form a carrier flow that flows through the respective channel 14 at a selected flow rate. The carbon dioxide flows through a heat exchanger 36 is chilled with a recalculating cooling bath 35 and is pumped via a $CO_2$ pump 37 to a mixer 39. The flow of $CO_2$ can also be passed through a pulse damper to minimize any pulsation caused by the pump 37. The modifier solvent flows through a solvent pump 41 into the mixer 39 where the solvent is mixed with the carbon dioxide. The carbon dioxide and solvent mixture then flows to a sample injection valve 43, where the sample 12 is received from the autosampler 21 is combined with the carrier flow to form the sample flow 31.

The sample flow 31 is passed through a heat exchanger 45 at which time the fluid becomes supercritical, and then a separation media, such as an SFC column 32, that separates the sample components within the sample flow 31. Accordingly, each sample component is spaced apart from the other components as the sample flow exits the SFC column 32 and moves through the purification channel 14.

Figure 4:
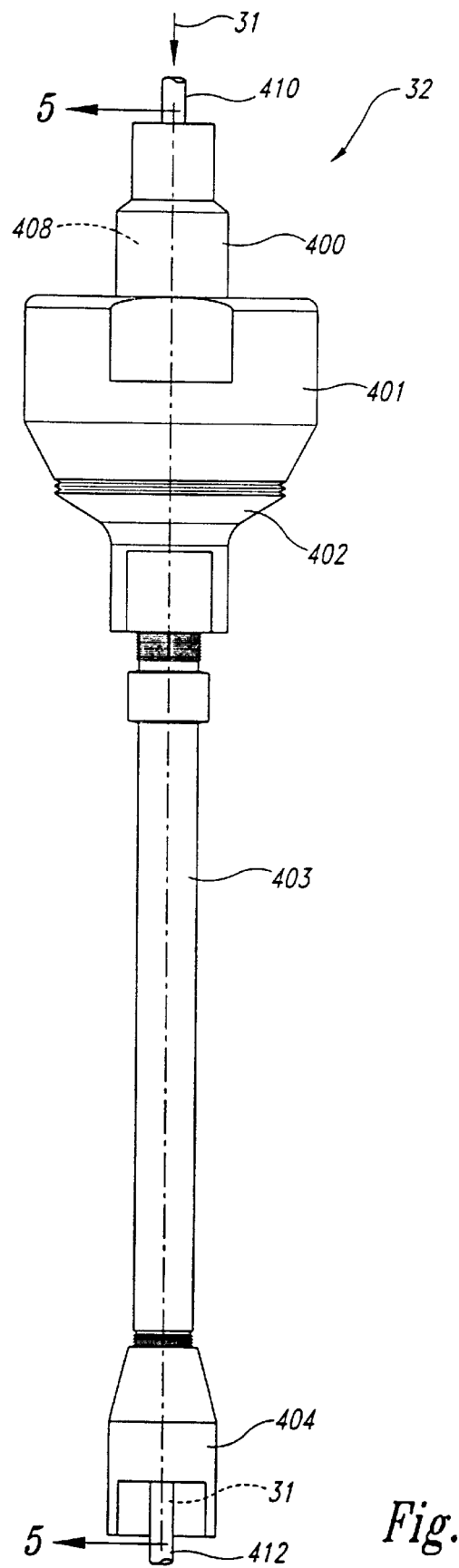
FIG. 4 shows a side elevation view of a two-piece column of the purification system of FIG. 3.
Figure 5:
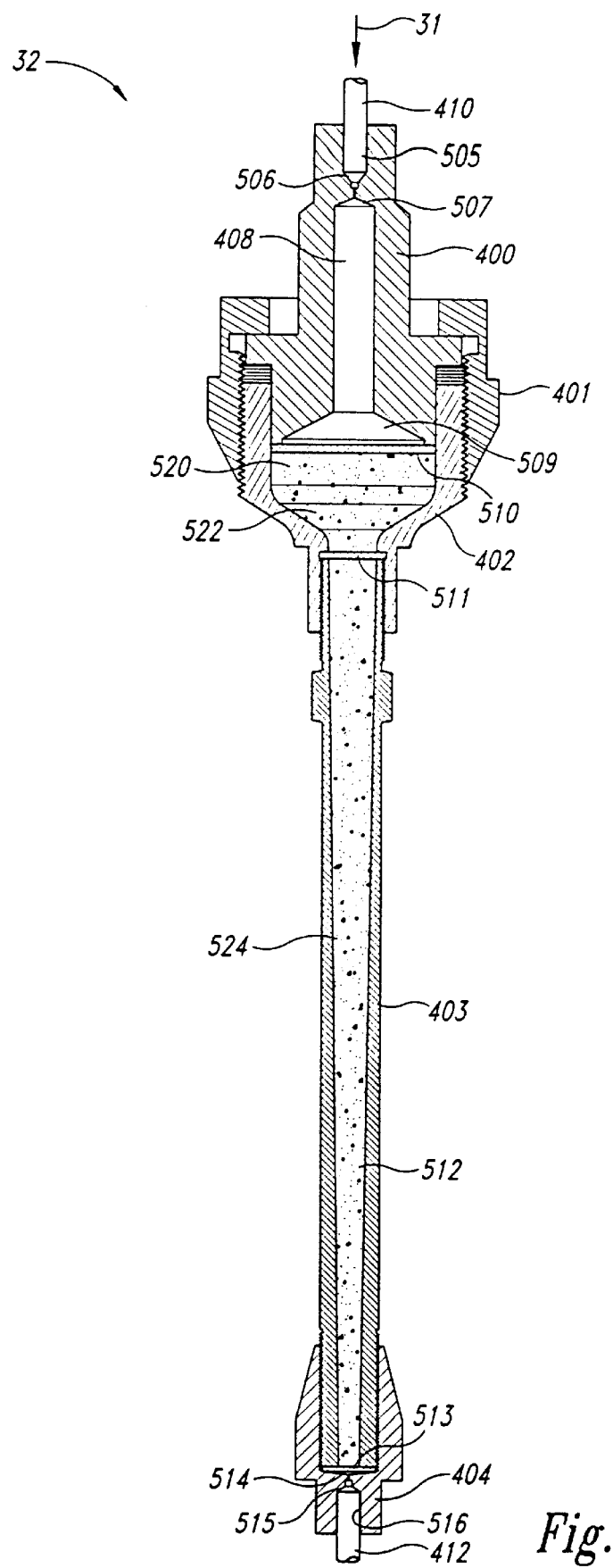
FIG. 5 shows a cross-sectional view of the two-piece column taken substantially along line 5—5 of FIG. 4.

In one embodiment of the invention, the column 32 is a two-piece column, as illustrated in FIGS. 4 and 5, for use in supercritical fluid chromatography. As best seen in FIG. 4, the components of the column 32 include an upper dilution body 400 that defines that a dilution chamber 408 therein. The top portion of the dilution body 400 is connected to an inlet tube 410 through which the sample flow 31 passes and moves into the column 32. The upper dilution body 400 is connected to a loading body 402 and securely retained in place by a top end cap 401 The dilution chamber body 400 is compressed downwardly by the top end cap 401 that screws externally onto the threads of the loading body 402. In an alternate embodiment for use in liquid chromatography, the dilution chamber is not needed, so the column 32 does not include the dilution body attached to the loading body.

The dilution chamber body 400, the top end cap 401, and the loading body 402 of the illustrated embodiment are made from an inert material, such as stainless steel. In alternate embodiments, other inert materials can be used for construction of the column's components. A separation body 403 at its upper end is attached to the lower portion of the loading body 402. The lower end of the separation body 403 is securely connected to a bottom end cap 404 that connects to an outlet tube 412, through which the separated sample flow 31 exits the column 32.

As best seen in a cross-sectional view of FIG. 5, the sample flow 31 enters the column 32 at a top-threaded port 505 to which an inlet tube 410 is sealed by an external ferrule that seats onto the top ferrule sealing point 506 in the threaded port. The sample flow is directed radially from the inlet tube 410 into the upper dilution chamber 408 by means of an inverted top funnel portion 507. The top funnel portion 507 is substantially conical in geometry and it defines the top of the dilution chamber 408. The main body of the dilution chamber 408 is substantially cylindrical, although it can be constructed with other geometric shapes in alternate embodiments. The bottom of the dilution chamber 408 has an inverted bottom funnel portion 509 that flares radially outwardly from the dilution chamber's main body. Accordingly, the bottom funnel portion 509 flares to a lower opening having a greater diameter than the dilution chamber's main body. The lower opening of the bottom funnel portion 509 is positioned over a top frit 510 located below the dilution chamber 408.

The dilution chamber's entire volume is void of stationary phase material. Dilution of the sample in the sample flow takes place in the dilution chamber 408 as the sample flow moves downwardly through the main body to the bottom funnel portion 509, where the sample flow passes through the top frit 510. The top frit 510 distributes the sample over a column bed 512 in a loading region 520 directly below the top frit 510. Sealing of the dilution chamber 408 is achieved at the top frit 510 where the dilution chamber body 400 fits internally into the loading body 402.

The loading body 402 has a loading region 520 below the top frit 510 and a transition region 522 below the loading region. The loading and transition regions 520 and 522 in the loading body 402 are filled with a stationary phase material, such as cyano, that defines a column bed 512 in the column 32. In alternate embodiments, other stationary phase materials can be used to form the column bed 512. The loading region 520 has an inner diameter approximately two or more times greater than the inner diameter of the separation region 524, and a length of approximately one-half or less than the length of the separation region. In the loading region 520, the sample flow traverses downwardly through the column bed 512 into the transition region 522, which has a conical shape as defined by the loading body 402. The transition region 522 directs the sample flow into the separation region 524 of the column bed 512.

The top of the separation body 403 is threadably attached to the bottom of the loading body 402 by a threaded connection and is sealed by an adjoining frit 511 sandwiched therebetween. The separation body 403 of the illustrated embodiment is made of stainless steel and is shaped so the interior chamber containing the separation region 524 of the column bed 512 has a tapered cylindrical geometry with a wider upper end and a narrower lower end. The interior chamber of separation region 524 of the column bed 512 is filled with the stationary phase material. The sample flow travels downwardly through the column bed 512 in the separation region 524 past a bottom frit 513 and onto a bottom fluid funnel 514 formed in the bottom end cap 404. The bottom of the separation region 524 is sealed by the bottom end cap 404 screwed externally onto the separation body 403. The bottom frit 513 is sandwiched between the bottom end cap 404 and the separation body 403. The bottom fluid funnel 514 is conical and directs the fluid into a bottom threaded port 516 formed in the bottom end cap 404 to which the outlet tube 412 can be screwed. The outlet tube 412, when screwed into the outlet port 516, is sealed against the bottom end cap 404 at a bottom ferrule sealing point 515 by use of an external ferrule.

Figure 6:
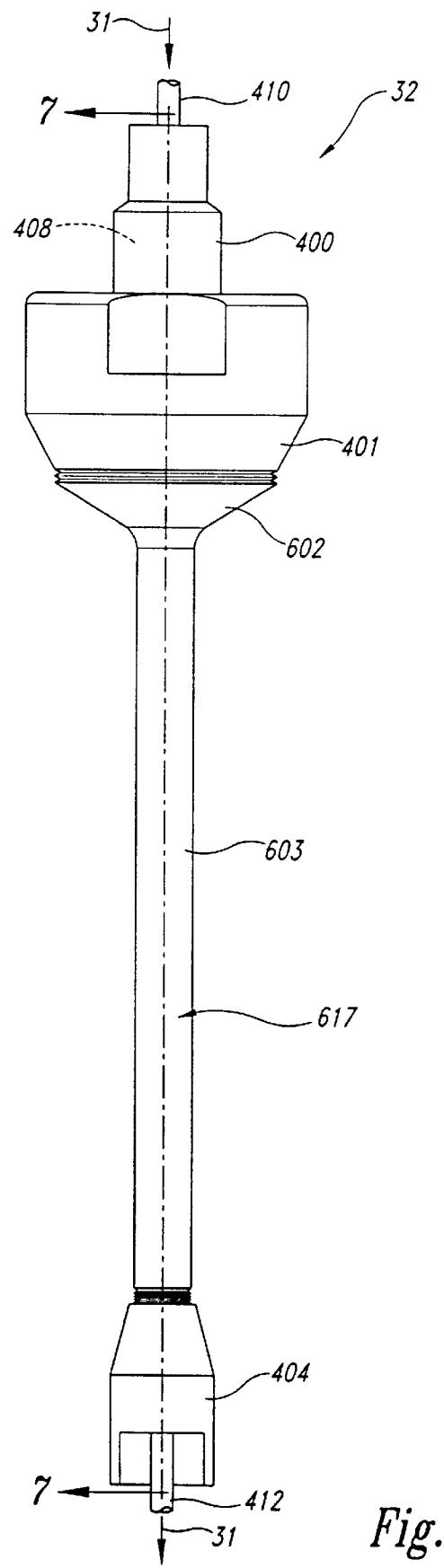
FIG. 6 shows a side elevation view of a one-piece column in accordance with an alternate embodiment of the invention.

In an alternate embodiment illustrated in FIG. 6, the column 32 is a "one-piece" column. In view of the similarities between the two embodiments, components that are the same between the two embodiments are identified in the figures by the same reference numbers for purposes of clarity. The one-piece column is substantially the same as the two-piece column discussed above, with the exception that the loading body 602 and the separation body 603 are integrally formed from a single stainless steel unit to define a One-Piece Loading and Separation (OPLAS) body 617. Accordingly, the upper frit 511 used in the two-piece column is not needed and thus omitted.

Figure 7:
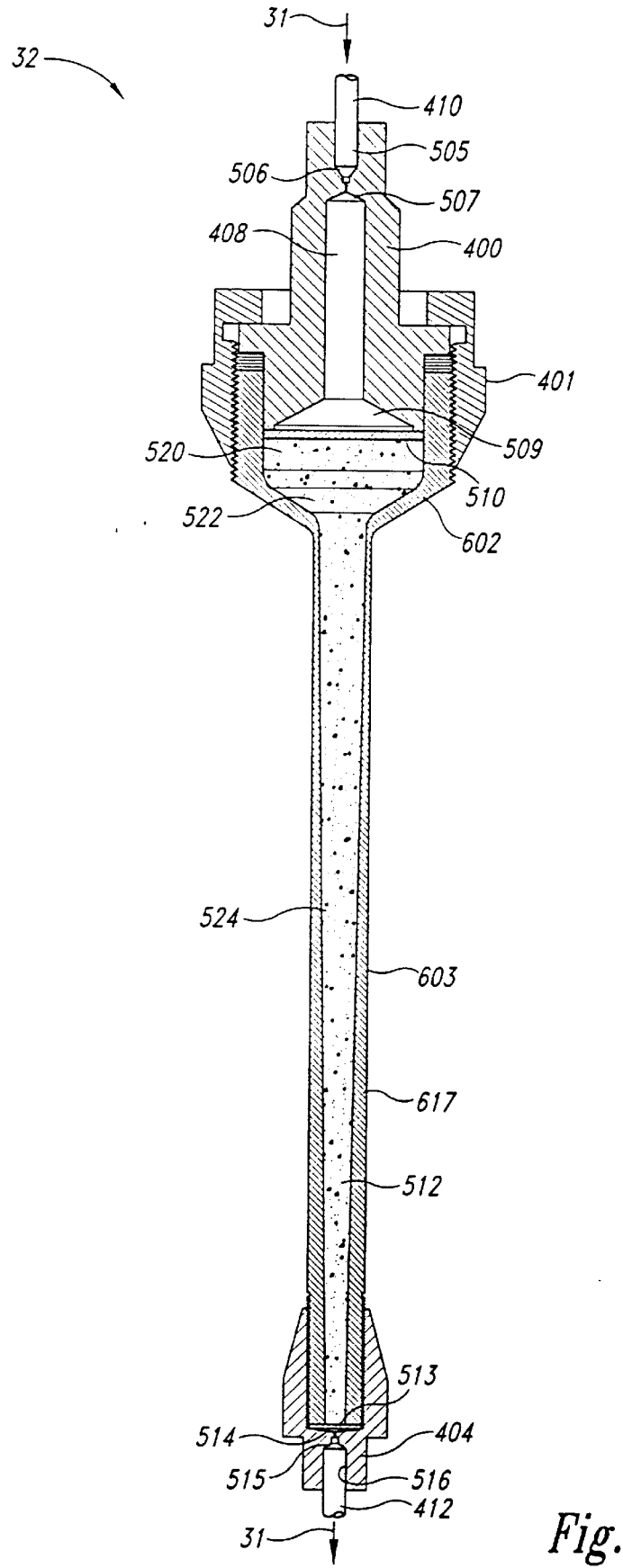
FIG. 7 shows a cross-sectional view of the one-piece column taken substantially along line 7—7 of FIG. 6.

As best seen in the cross-sectional view of FIG. 7, the dilution chamber body 400 fits internally into the OPLAS body 617 and is secured by the top end cap 401 that screws externally onto the OPLAS body. The lower end of the OPLAS body 617 screws internally into the bottom end cap 404. Accordingly, the loading region 520 formed in the OPLAS body 517 has a diameter approximately two or more times greater than the inner diameter of the separation region 524, and a length of approximately one-half or less than the length of the separation region.

Figure 8A:
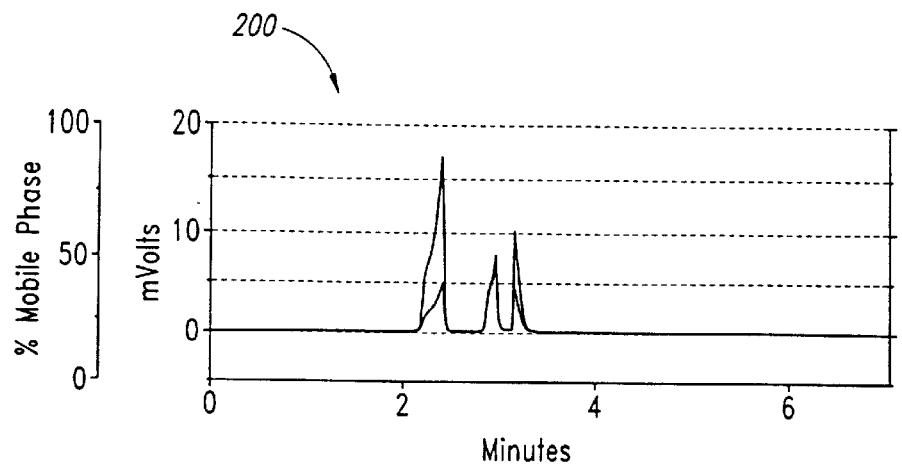
FIGS. 8A–C show results of three chromatographic runs showing the improvement over prior art.
Figure 8B:
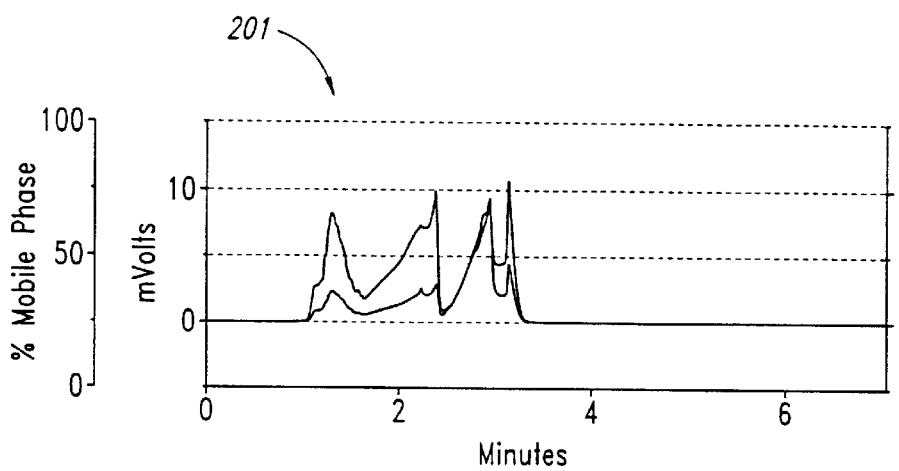
Figure 8C:
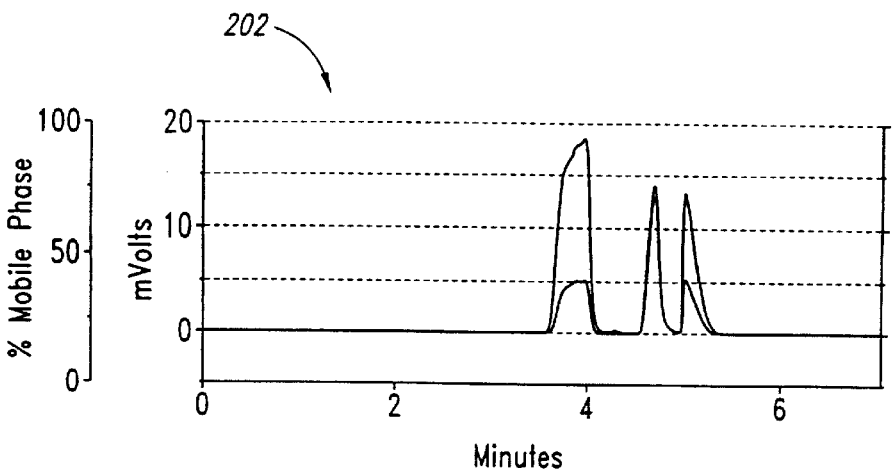

FIGS. 8A–C show graphical results from three chromotographic runs showing improvement over the prior art provided by the column 32 in accordance with the present invention. All three chromotographic runs were injected with the same mass loading of a three-compound mixture and run under the same chromotographic conditions. Run 200 (FIG. 8A) shows the separation results using a single prior art column injected with a small volume solvent mixture. Run 201 (FIG. 8B) shows the separation results using the same prior art single column as in run 200, wherein the prior art column was injected with a large volume solvent mixture. Run 202 (FIG. 8C) shows the separation results using a two-part column 32 in accordance with an embodiment of the present invention as discussed above. Run 202 was injected with the same large volume solvent mixture as run 201.

The first portions of the column 32 (e.g., the loading and transition portions) have a larger inner diameter than the column's second portion (the separation region) and a shorter length than the column's second portion. Accordingly, the column 32 in accordance with the present invention can handle large volume solvent mixtures with multiple compounds and provide highly accurate separation and detection of the different compounds, such as by use of a mass spectrometer or the like. This accuracy in conjunction with corresponding speed for handling large volume solvent mixtures with multiple compounds provides a faster and more efficient processing capability.

Referring again to FIG. 3, the sample flow 31 exits the SFC column 32, flows through another heat exchanger 47, and flows to a detector 34. The detector 34 is adapted to detect the different components or peaks in the sample flow 31 that have been separated from each other by the SFC column 32. In the illustrated embodiment, the detectors 34 are ultraviolet light (UV) detectors. While UV detectors are used in the illustrated embodiment, other detectors can be used, such as infrared (IR) detectors or any other suitable detector capable of identifying a peak within the sample flow 31.

Each detector 34 is coupled to the common computer controller 18. When the detector 34 identifies a peak, the detector provides a signal to the computer controller 18 indicating the peak. Because the sample flow rate is known in each channel 14, the computer controller 18 can calculate the location of each peak within each channel 14 as the sample flow 31 moves trough the channel. As an example, when two peaks are detected in the same sample flow 31, the computer controller 18 calculates and monitors where those peaks are within the channel 14. The computer controller 18 also calculates where the peaks are relative to each other during the entire purification process.

As the sample flow 31 moves through the purification channel, it is in a vaporous state. After the sample flow 31 exits the detector 34, additional solvent, referred to as makeup solvent 49, is added to the sample flow as needed to increase the volume of liquid in the sample flow to facilitate transport of the sample to the fraction collector assembly (discussed below). The makeup solvent 49 is pumped from a solvent container by solvent pumps 51 into the respective purification channel 14. The solvent container and the solvent pumps 51 are each coupled to the computer controller 18 so the computer controller can monitor the solvent volumes used and can control the solvent pumps as necessary for the selected purification run. The computer controller 18 also monitors the amount of makeup solvent 49 needed within the purification channel during a run, so it can detect if a potential problem arises, and can provide an alarm or other warning to an operator of the system.

After any of the makeup solvent 49 is added to the sample flow 31, the sample flow passes through a back pressure regulator module 53 in a back pressure regulator assembly 55. The back pressure regulator module 53 detects and controls the back pressure within the channel 14 to maintain the desired pressure within the channel.

As best seen in FIG. 9, the back pressure regulator assembly 55 includes a housing 900 that removably retains four back pressure regulator modules 53, one for each purification channel 14. The assembly 55 also includes a communication panel 902 to which the back pressure regulator modules 53 attach for communication to and from the computer controller 18 (FIG. 3). The modules 53 plug into the housing 900 and onto the communication panel 902. Accordingly, if a new or substitute module 53 is needed in the purification system, it can be installed quickly and easily upon unplugging one module and plugging in the replacement module.

Figure 10:
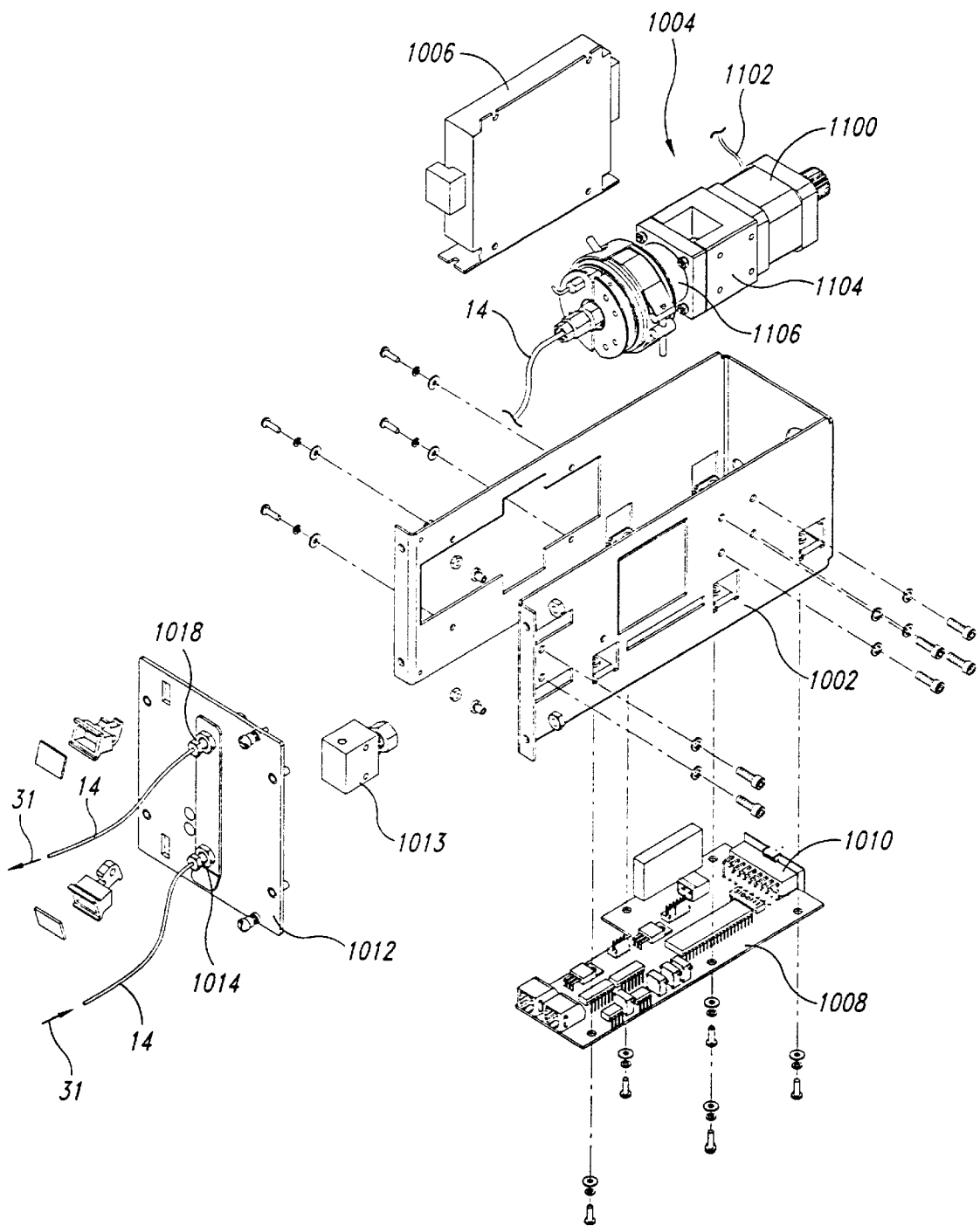
FIG. 10 is an enlarged exploded isometric view of a back pressure regulator module from the assembly of FIG. 9.

As best seen in FIG. 10, the pressure regulator module 53 includes a housing 1002 that contains and protects a regulator assembly 1004. The regulator assembly 1004 controls the back pressure in the sample flow as it moves through the respective purification channel 14. The regulator assembly 1004 is electrically connected to a stepper motor controller 1006 which activates and adjusts the regulator assembly as needed during a purification run. The stepper motor controller 1006 is connected to a printed circuit board 1008 which also attaches to the housing 1002. The printed circuit board 1008 includes a plurality of connectors 1010 that releasably plug into the communication panel 902 (FIG. 9) of the regulator assembly. Accordingly, communication to and from the computer controller 18 is provided to the pressure regulator module 53 through the printed circuits board and to the regulator assembly 1004 via the stepper motor controller 1006.

The pressure regulator module 53 also includes a front faceplate 1012 that mounts to the housing 1002. The front faceplate 1012 has an inlet port 1014 into which the tubing of the purification channel extends so as to allow the sample flow 31 to pass into the pressure regulator module 53. The sample flow passes through a pressure sensor 1013, which is also coupled to the printed circuit board 1008, so as to identify the sample flow's pressure. After the sample flow 31 enters the regulator assembly 1004 and the sample flow's pressure is modified as needed, as discussed in greater detail below, the sample flow exits the pressure regulator module 53 through an outlet port 1018 on the front faceplate 1012.

Figure 11:
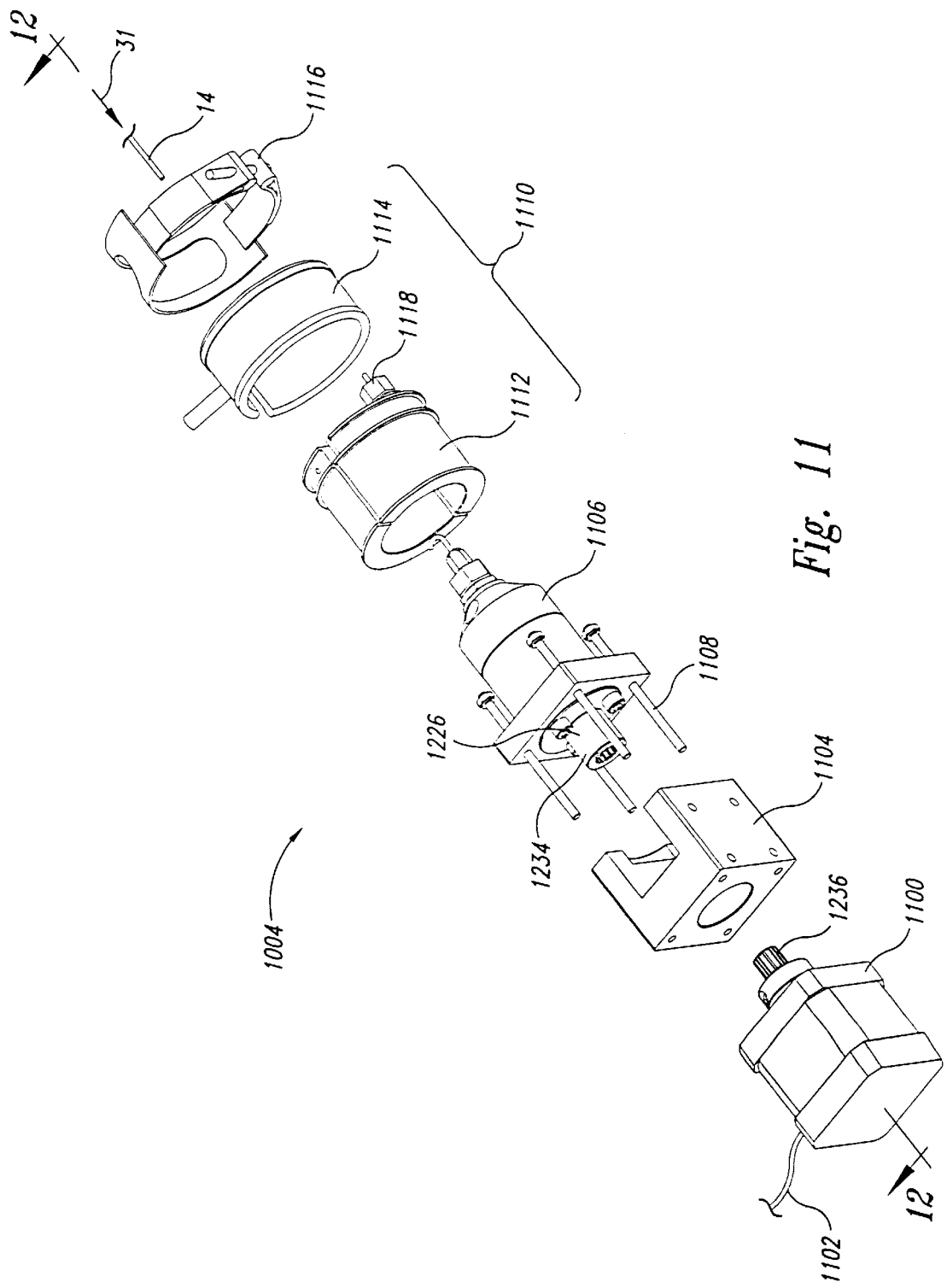
FIG. 11 is an enlarged isometric view of a regulator/motor assembly of the back pressure regulator module of FIG. 10.
Figure 12:
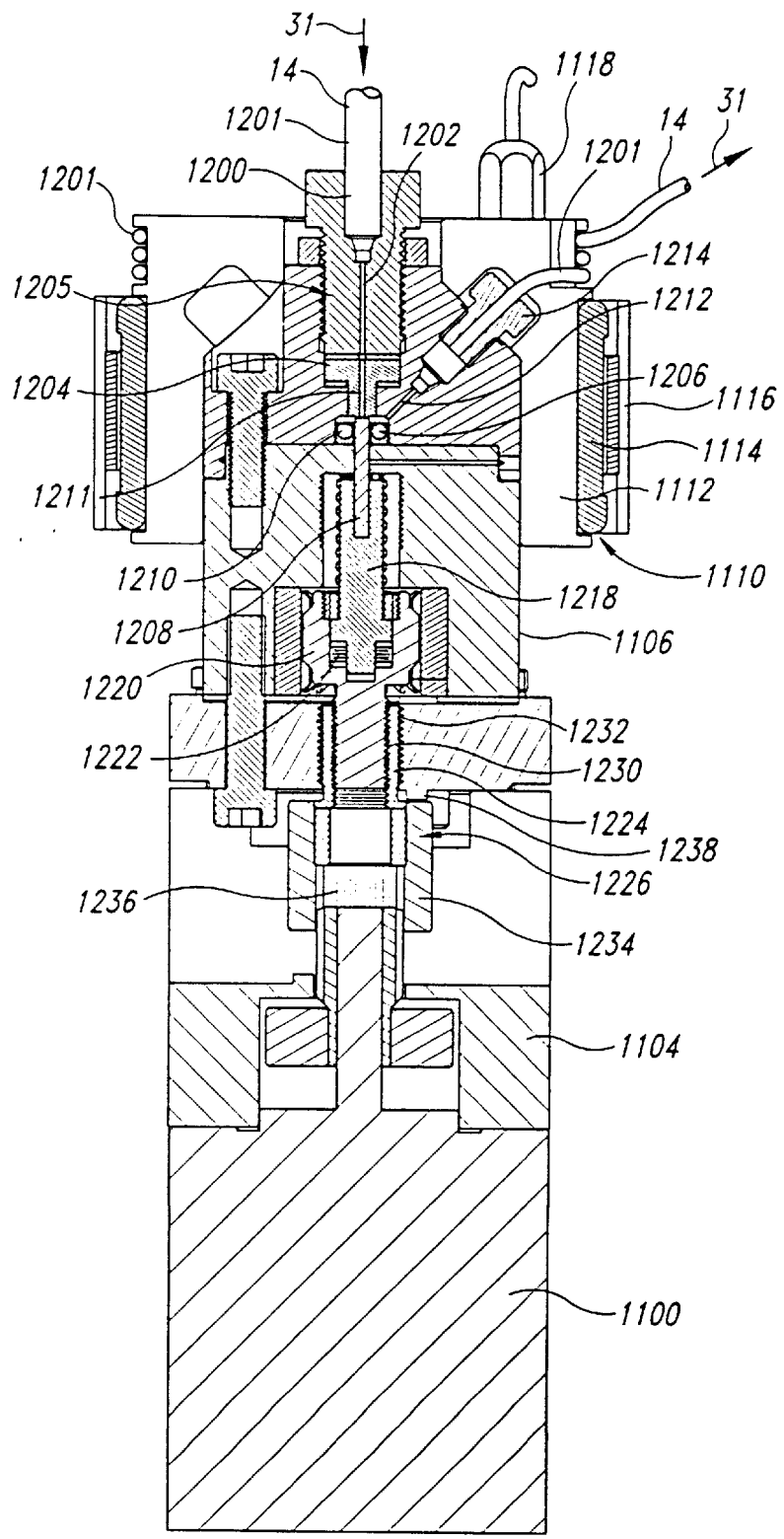
FIG. 12 is an enlarged cross-sectional view of the regulator assembly taken substantially along line 12—12 of FIG. 11.

As best seen in FIGS. 11 and 12, the regulator assembly 1004 includes a stepper motor 1100 having wiring 1102 that connects to the stepper motor controller 1006 (FIG. 10). The stepper motor 1100 is connected to a motor mount 1104 that interconnects the stepper motor to a back pressure regulator 1106. The back pressure regulator 1106 is securely retained to the stepper motor 1100 by a plurality of mounting screws 1108 that extend through the motor mount 1104 and screw into the housing of the stepper motor 1100.

The regulator assembly 1004 also includes a heater 1110 adapted to heat the sample flow 31 within the purification channel's tubing so as to prevent formation of ice crystals or the like that may occur as a result of pressure differentials occurring across the pressure regulator. The heater 1110 includes a heat transfer body 1112 that extends over the back pressure regulator 1106 and a heater band 1114 clamped onto the heat transfer body by a band clamp 1116. The heater band 1114 is coupled to the computer controller 18 to allows the heater band to regulate its temperature to provide different heating configurations to the back pressure regulator during a purification run. The heat transfer body 1112 includes a temperature sensor 1118 that monitors the temperature of the heat transfer body during the purification run. The temperature sensor 1118 is coupled to the computer controller 18 (FIG. 3) so the computer controller can regulate the heat provided from the heater band 1114 as needed during operation of the regulator assembly 1004.

As best seen in FIG. 12, the regulator 1106 has an inlet port 1200 that receives the purification tube 1201 carrying the sample flow 31. The inlet port 1200 has an inlet channel 1202 that communicates with a nozzle 1204 positioned below the inlet port. The nozzle 1204 in the illustrated embodiment is a ceramic component having a diamond coating so as to provide an extremely hard and durable nozzle within the regulator. The nozzle 1204 is exposed to very harsh conditions, including caustic solvents and pressures of approximately 2000 psi or greater. The inlet port 1200 is threadably connected to the nozzle retainer 1205 so the inlet port is easily removable to provide access to the nozzle 1204 if replacement of a nozzle is necessary.

The nozzle 1204 includes an inlet channel 1211 extending therethrough that communicates with a very small chamber that receives the sample flow 31 from the nozzle's inlet channel. The lower end of the inlet channel 1211 forms a nozzle orifice through which the sample flow passes. A stem 1208 positioned below the nozzle 1204 extends through a seal 1210, into the small chamber 1206, and terminates immediately adjacent to the nozzle orifice at the lower end of the inlet channel 1211. The stem 1208 is moveable relative to the nozzle orifice so as to adjustably close the flow path through the regulator 1206. In the illustrated embodiment, the stem 1208 is a sapphire stem. In alternate embodiments, the stem 1208 can be made of other very hard materials, such as diamond, ruby or the like. The stem 1208 is movable relative to the nozzle 1204 to adjust the opening size so as to regulate the pressure of the sample flow 31.

The sample flow 31 moves from the nozzle 1204 through the orifice and into an outlet channel 1212 that is in fluid communication with the small chamber 1206. The outlet channel 1212 extends through an outlet port 1214 that receives the exit tube 1201 therein so as to carry the sample flow 31 out of the regulator 1106. The exit tube 1201 extends from the outlet port 1214 and wraps around the heat transfer body 1112 approximately two times so the exit tube is heated, thereby preventing the formation of ice crystals within the purification tube and condensation on the outside of the exit tube. The purification tube 1201 then extends from the heat transfer body 1112 away from the regulator assembly and to the outlet port 1018 on the regulator module's faceplate 1012 (FIG. 10) as discussed above.

In the illustrated embodiment, the stem 1208 is a sapphire stem having, hardness characteristics suitable for use in the high pressure and harsh environment within the regulator assembly 1004. The sapphire stem 1208 is connected at its lower end to a rod 1218 movably positioned within a holding member 1220 having a threaded lower end. The holding member 1220 contains a biasing member 1222, such as Bellville washers, wave washers, or the like, that bias the rod 1218 and the stem 1208 toward the nozzle 1204. In the event the stem 1208 directly engages the nozzle 1204 or is subjected to an extremely high pressure pulse, the biasing member 1222 will compress so as to avoid damaging the sapphire stem 1208 or the nozzle 1204 during operation. The biasing member 1222, however, has a sufficient spring stiffness so it is not compressed during normal pressures of the sample flow within the tubing of the purification channel 14 during a purification run.

Adjustment of the regulator assembly 1106 is provided by dual concentric screws that move the stem 1208 relative to the nozzle 1204. As best seen in FIG. 12, the holding member 1220 is threaded into internal threads 1230 formed in a shaft 1224 of an adjustment screw 1226. In the illustrated embodiment, the internal threads 1230 have a pitch of 28 threads per inch (tpi). The adjustment screw's shaft 1224 also has external thread 1232 that screw into a threaded aperture in the regulator body 1106. In the illustrated embodiment, the external threads 1232 have a pitch of 27 tpi. Accordingly, the external threads 1232 of the adjustment screw 1226 have a thread pitch different than the pitch value of the internal threads 1230. The internal and external threads 1230 and 1232 are both right-handed pitch threads oriented in opposing directions so as to form the dual concentric adjustment screw configuration for attenuated movement of the stem 1208 relative to the nozzle 1204 for each turn of the adjustment screw.

The adjustment screw 1226 has an internal driving spline 1234 that securely engages a drive spline 1236 on the stepper motor 1100. The drive spline 1236 is press fit into the internal driving spline 1234. When the stepper motor 1100 is activated by the computer controller 18 (not shown), the driving spline 1236 rotates, thereby rotating the adjustment screw 1226. As the adjustment screw 1226 rotates one revolution, the dual concentric screw configuration counteracts the range of motion of the holding member 1228, and thus the stem 1208. As an example, if the stepper motor 1100 rotates the adjustment screw one full revolution, the holding member 1220 moves only one pitch value because of the pitch differentiation between the internal and external threads 1230 and 1232.

In one embodiment, one revolution of the adjustment screw along the external threads 1232 would move the adjustment screw 1226 and the holding member 1220 approximately b 0.0373inches. The internal threads 1230, however, move in the opposite direction approximately 0.03571 inches, resulting in a net movement of approximately 0.0013 inches. Accordingly, the dual concentric screw configuration within the regulator 1106 provides for extremely accurate and fine adjustments of the stem 1208 relative to the nozzle 1204 to closely control pressure regulation within the sample flow 31 as it passes through the back pressure regulator assembly 1004.

The back pressure regulator 1004 is formed with a minimum amount of dead volume and unswept volume within the purification channel extending therethrough to prevent or minimize the risk of cross contamination between purification runs for different samples. The back pressure regulator assembly is constructed with extremely durable components that will withstand the harsh environments experienced during the purification run at very high pressures, while providing sufficient safety characteristics to avoid damaging the back pressure regulator in the event of pressure spikes or the like.

In one embodiment, the stepper motor includes a rotational stop 1238 that prevents travel of the drive spline 1236 and, thus, the adjustment screw 1226 past a selected position relative to the regulator. The travel stop 1238 is positioned to block the stepper motor from driving the sapphire stem 1208 too far relative to the nozzle 1204, thereby preventing damage from overdriving from the stepper motor and crushing the sapphire stem against the nozzle.

The illustrated embodiment of the purification system utilizes the regulator assembly with the dual concentric screw configuration controlled by the computer controller 18. In alternate embodiments, the pressure regulator assembly 53 can be a stand alone regulator with selected control mechanisms.

As best seen in FIG. 3, the sample flow 31 travels from the pressure regulator assembly 55 to the microsample valve 38. The microsample valve 38 is operatively connected to the computer controller 18 and is activated by the computer controller when a peak in the sample flow 31 is moving past the microsample valve. Upon activation, the microsample valve 38 diverts a sampling from the sample flow 31 and directs it to the mass spectrometer 16 for analysis. The remaining portion of the sample flow 31 continues along the flow path of the respective channel 14 substantially uninterrupted. Each microsample valve 38 is activated so the sampling contains a selected portion of just the peak. The mass spectrometer 16 analyzes the sampling and determines whether the peak is a target compound or not.

As the four sample flows 31 moves simultaneously through the respective channels 14 and through the detectors 34, the peaks from the four channels will likely occur at separate times during the sample runs. Accordingly, the mass spectrometer 16 usually receives the samplings from the four channels with some time between the samplings. In some cases, however, two or more detectors 34 may detect a peak in its sample flow at the same time or at overlapping times during the sample run. The computer controller 18 is programmed with an analysis priority protocol that controls the activation sequence of the microsample valve 38 when peaks in the different channels 14 occur at the same time or overlapping times. Accordingly, the priority protocol controls the timing of when the samplings of the peaks are diverted to the mass spectrometer 16, so each peak can be analyzed separately by the same analyzer. In one embodiment, when a peak from separate channels 14 are detected simultaneously, the computer controller 18 activates the microsample valves 38 at different times so samplings of the respective peaks are sequentially directed to the mass spectrometer 16. Activation of each microsample valve 38 can be controlled by revising the computer controller's analysis priority protocol to provide sequential sampling.

Figure 13:
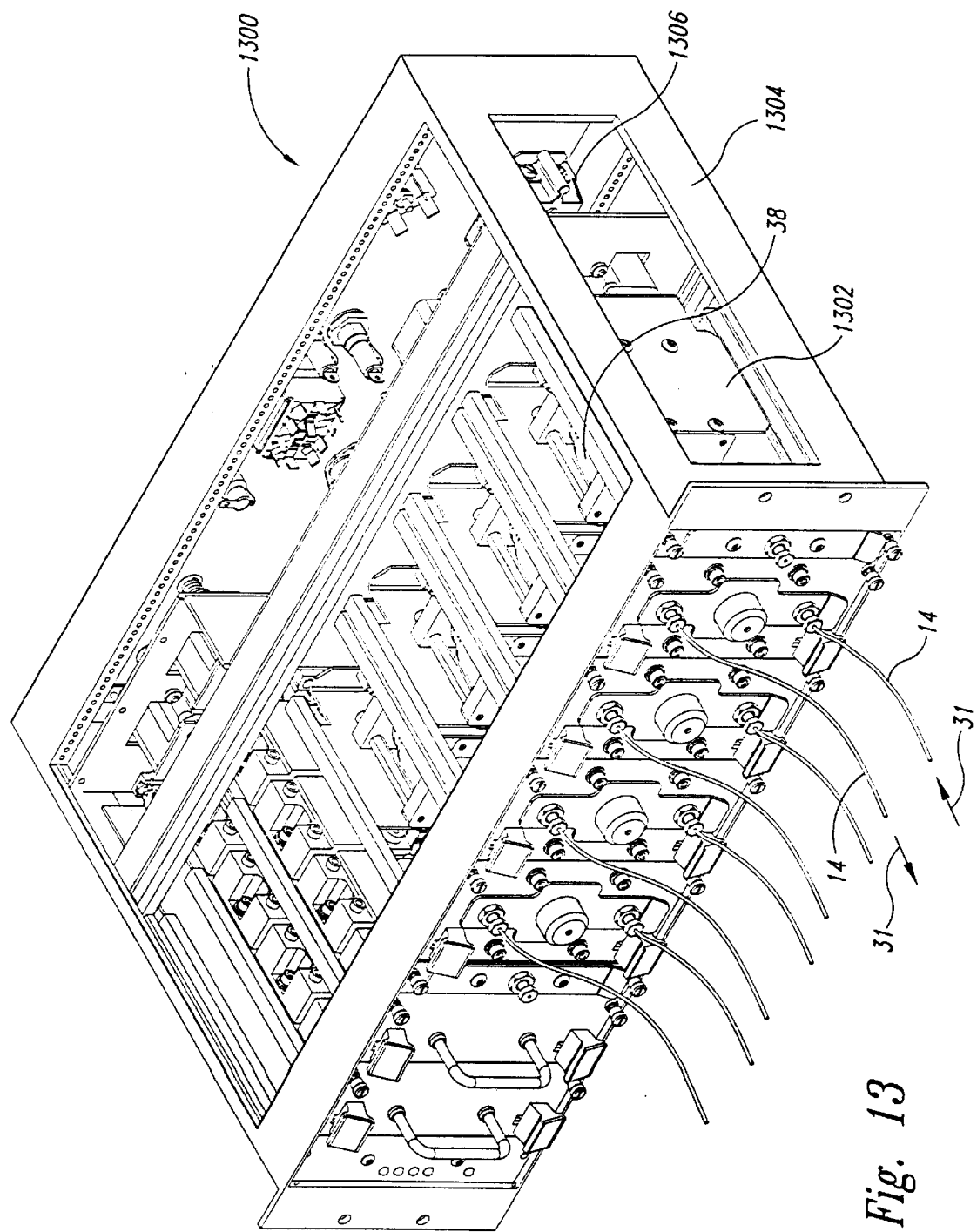
FIG. 13 is an enlarged isometric view of a microsample valve assembly from the purification system of FIG. 3.

As best seen in FIG. 13, the four microsample valves 38 are part of a microsample valve assembly 1300 that has four valve modules 1302. Each valve module 1302 contains a microsample valve 38 for its respective purification channel 14. The valve modules 1302 are removably received by a housing 1304 and plug into connectors coupled to a communication panel 1306. The communication panel 1306 is, in turn, coupled to the computer controller 18 (not shown), so the computer controller can control the activation of each microsample valve 38.

Figure 14A:
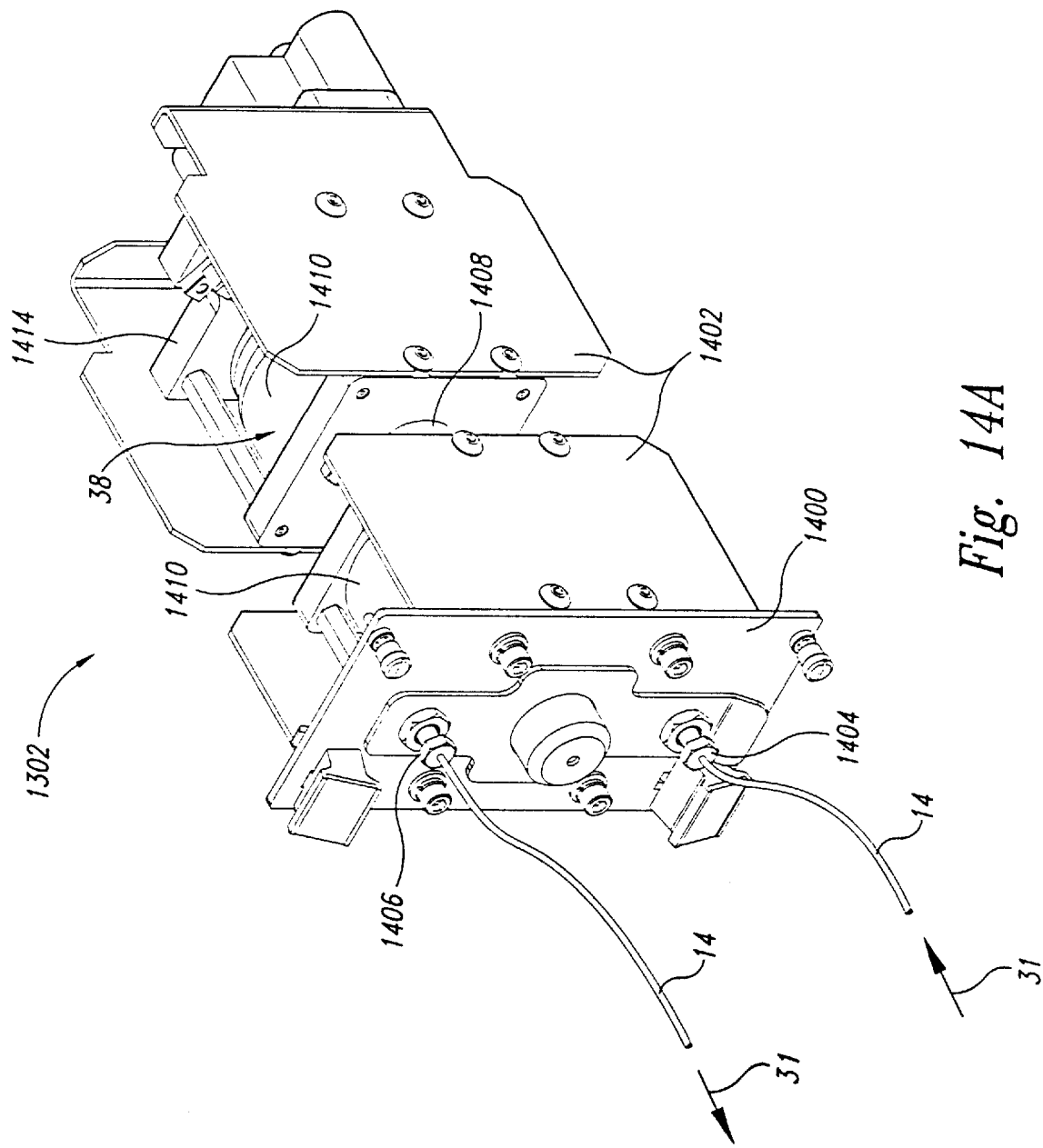
FIG. 14A is an isometric view of a microsample valve from the assembly of FIG. 13.
Figure 14B:
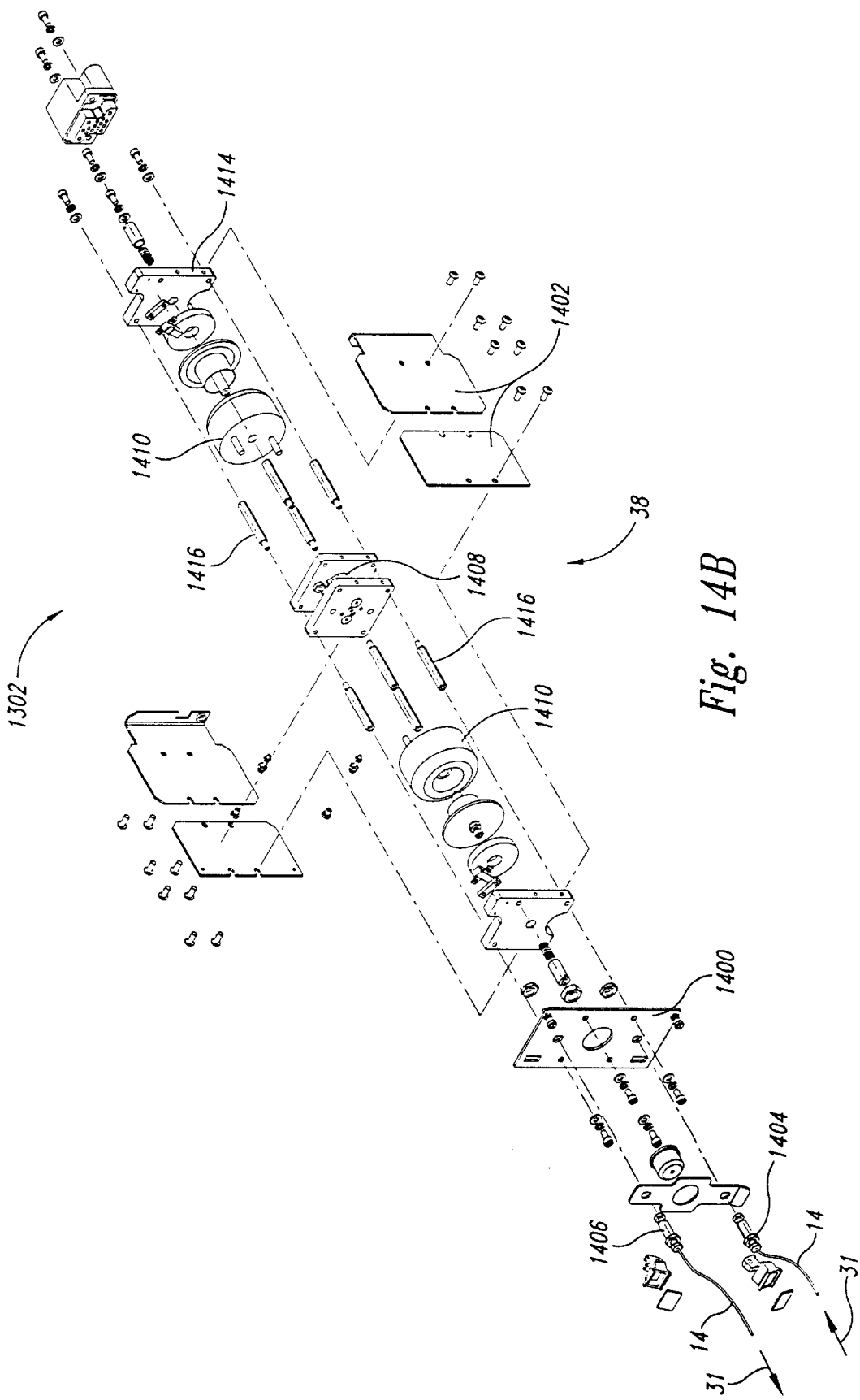
FIG. 14B is an enlarged, exploded isometric view of a microsample valve from the assembly of FIG. 13.

As best seen in FIGS. 14A and 14B, each valve module 1302 includes a faceplate 1400 and opposing side plates 1402 that securely engage the microsample valve 38. The faceplate 1400 has an inlet port 1404 and an outlet port 1406 that receive the purification channel's tubing and direct the sample flow into and out of the valve module 38.

The microsample valve 38 includes a valve body 1408 positioned between a pair of electromagnetic solenoids 1410. The solenoids 1410 are activatable by the computer controller 18 (not shown) to control activation of the microsample valve, as discussed in detail below. The solenoids 1410 are each sandwiched between the valve body 1408 and outer mounting plates 1414, and mounting screws 1416 secure the outer mounting plates to the valve body.

Figure 15:
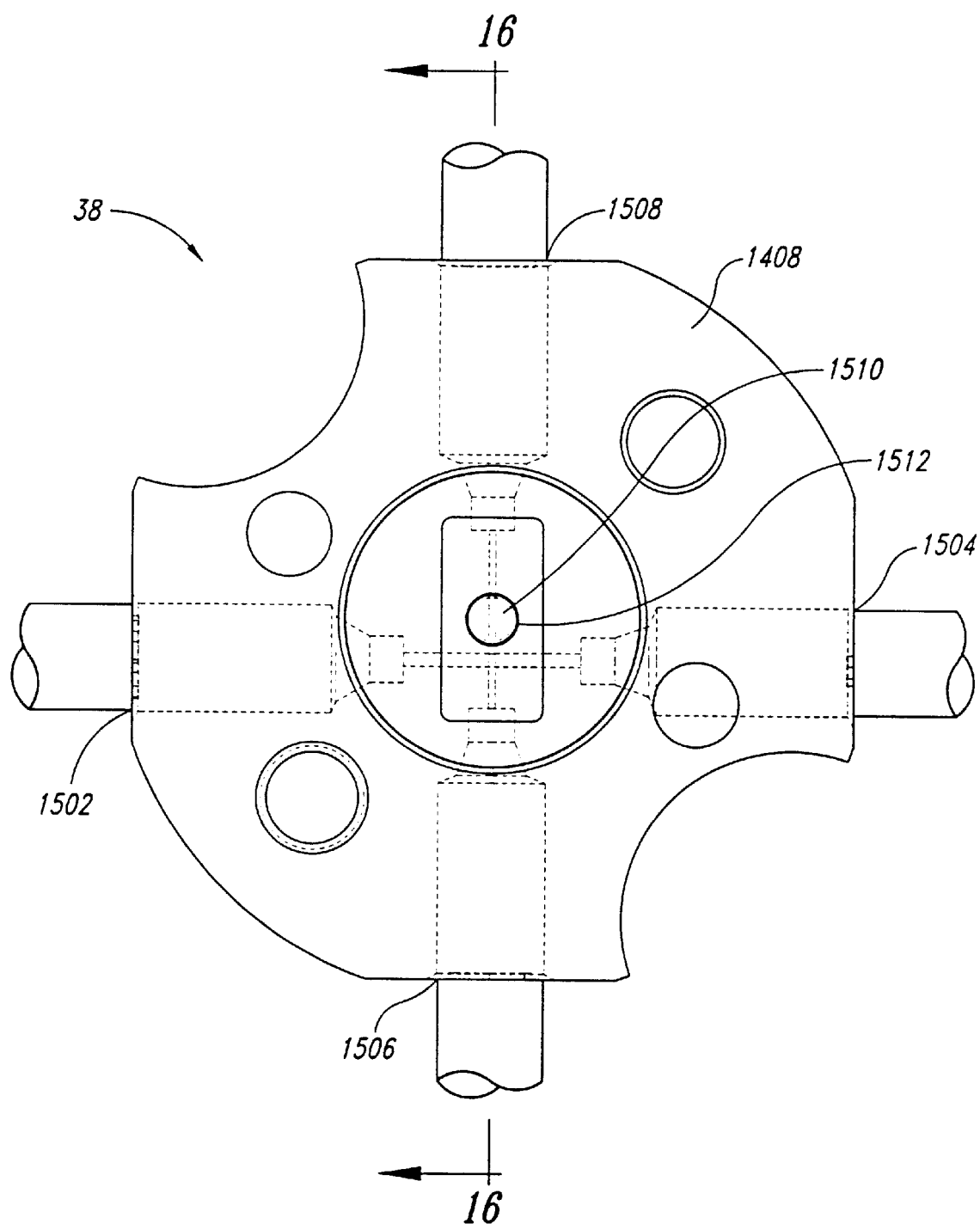
FIG. 15 is a plan view of a valve body of the microsample valve of FIG. 14.
Figure 16:
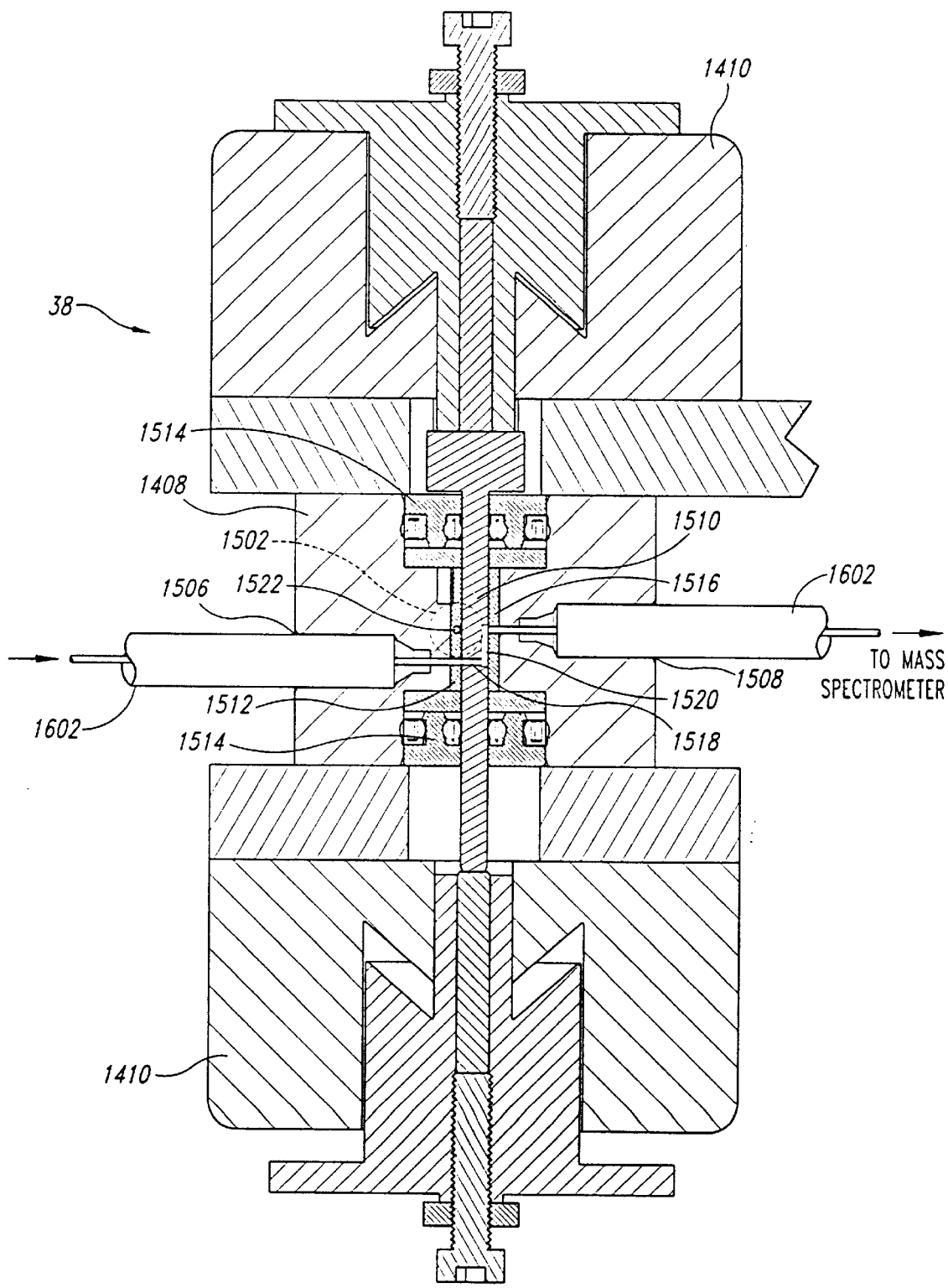
FIG. 16 is an enlarged cross-sectional view taken substantially along line 16—16 of FIG. 14, the microsample valve being shown in a non-sampling position.
Figure 17:
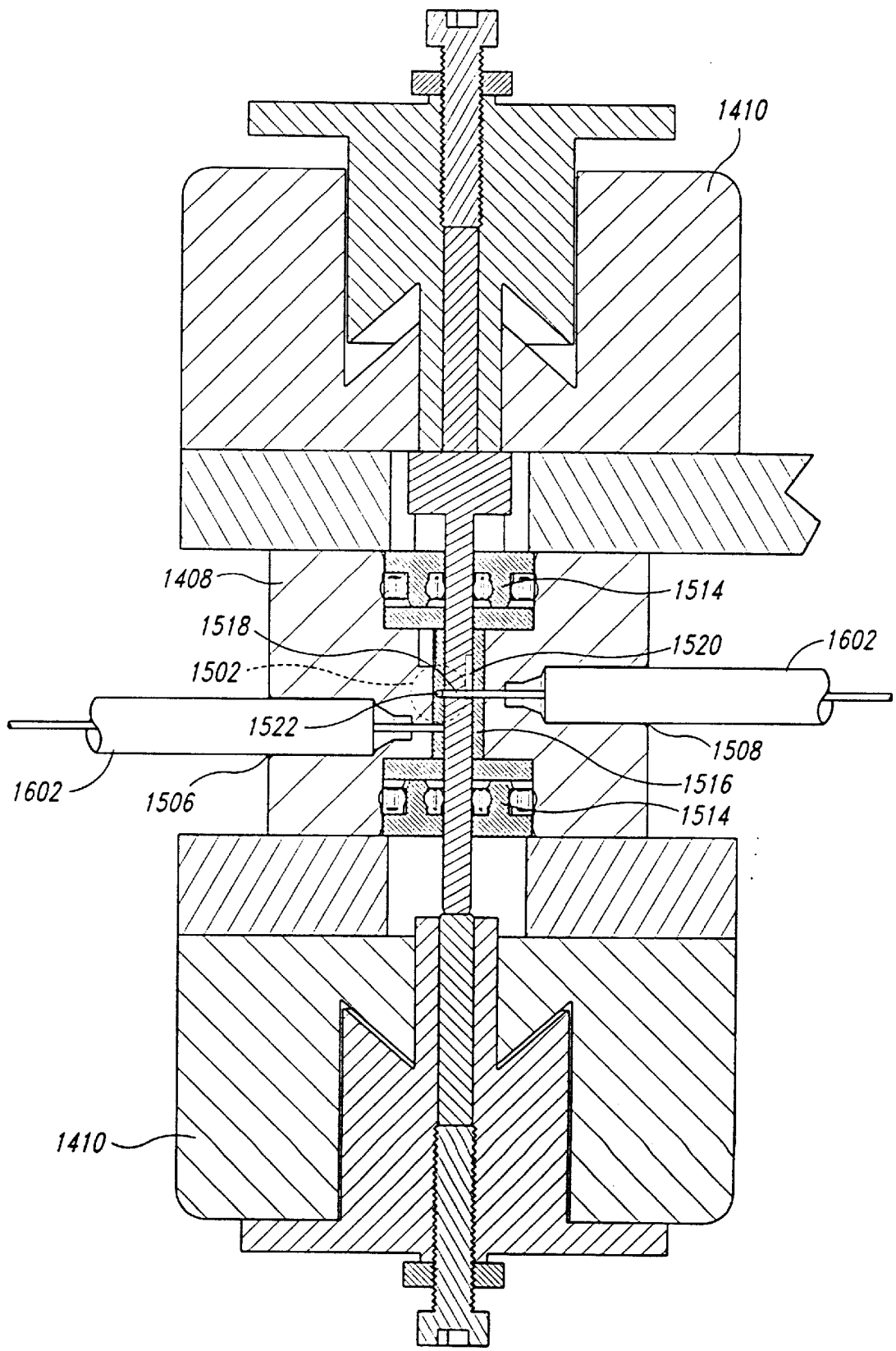
FIG. 17 is an enlarged cross-sectional view taken substantially along line 17—17 of FIG. 14, the microsample valve being shown in a sampling position.

As best seen in FIGS. 15–17, the valve body 1408 has a sample inlet port 1502, a sample outlet port 1504 (FIG. 15), a solvent inlet port 1506, and a flow outlet port 1508. The solvent inlet port 1506 is axially misaligned with the flow outlet port 1508. The flow outlet port 1508 is in fluid communication with the mass spectrometer 16, so fluid exiting the microsample valve 38 through the flow outlet port is carried to the mass spectrometer 16 (FIG. 3). The microsample valve 38 has a stem 1510 slidably disposed within an interior chamber 1512 in the valve body 1408. The stem 1510 slidably extends through the valve body 1408 and is connected at opposite ends to the electromagnetic solenoids 1410. The solenoids 1410 control the stem's axial position within the valve body 1408. The solenoids 1410 are connected to the computer controller 18 (FIG. 3), so the computer controller can control or adjust the stem's axial position. Upper and lower seals 1514 are positioned within the valve body 1408 adjacent to the solenoids 1410, and a center plastic sleeve 1516 extends between the upper and lower seals. The stem 1510 extends through the upper and lower seals 1514 and the plastic sleeve 1516 such that a fluid-tight seal is formed therebetween. In the illustrated embodiment, the stem 1510 is press fit into the plastic sleeve 1516, thereby preventing dead space around the stem.

As best seen in FIGS. 16 and 17, the stem 1510 has a through hole 1518 in fluid communication with the flow outlet port 1508 and to the mass spectrometer 16. The stem 1510 also has an axial groove 1520 on the outflow side of the valve body 1408 and in fluid communication with the flow outlet port 1508. The axial groove 1520 extends upwardly from the through hole 1518, along the stem's surface, and is sized to direct the fluid flow upwardly from the through hole along the groove between the stem's surface and the center plastic sleeve 1516. The through hole 1518 is shaped and sized to allow either a flow of carrier solvent or a sampling of a peak from the sample flow to pass toward the mass spectrometer 16.

Referring now between FIGS. 3, 15 and 16, the solvent inlet port 1506 (FIGS. 15 and 16) is connected to a carrier solvent line 1602 that connects to a carrier solvent source 1604 (FIG. 3) and a carrier solvent pump 1606. The carrier solvent pump 1606 is also coupled to the computer controller 18 that controls the flow of carrier solvent to the microsample valves 38. A substantially continuous flow of carrier solvent is provided to the microsample valves 38 during a purification run. In the illustrated embodiment, the carrier solvent line 1602 connects to all four microsample valves 38 in series, so the carrier solvent will flow through all of the microsample valves and to the mass spectrometer. Accordingly, the carrier solvent enters the first microsample valve 38 through the solvent inlet port 1506 (FIGS. 15 and 16), exits through the flow outlet port 1508 (FIG. 16), back into the carrier solvent line 1602, and into the next microsample valve through its solvent inlet port. The flow continues through each microsample valve 38 and then to the mass spectrometer 16.

The microsample valve 38 in each purification channel 14 also has a continuous flow of the sample flow 31 passing through it. The sample flow 31 enters the microsample valve 38 through the sample inlet port 1502 (FIGS. 15 and 16), through a sample line 1522 extending through the valve body 1408 immediately adjacent to the stem 1510, and out through the sample outlet port 1504. Accordingly, the sample flow 31 in the illustrated embodiment is transverse to the flow of the carrier solvent.

When the microsample valve 38 is in a lowered normal position, shown in, FIG. 16, the through hole 1518 is below and out of communication with the sample flow 31. The stem 1510 blocks the sample flow 31 from passing through the flow outlet port 1508 to the mass spectrometer 16 (FIG. 3). When the stem 1510 is in the lowered position, a continuous flow of carrier solvent passes into the valve body 1408 through the solvent inlet port 1506, through the through hole 1518, up the axial groove 1520, and out of the valve body 1408 through the flow outlet port 1508 toward the mass spectrometer 16.

During normal use, when a peak has not been identified, the microsample valve 38 remains in this lowered normal position, so only the carrier solvent flows through the microsample valves to the mass spectrometer 16. When the detector 34 (FIG. 3) detects a peak in the sample flow 31 and the computer controller 18 activates the microsample valve 38, the solenoids 1410 immediately move the stem 1510 axially from the lowered position to a raised sampling position, shown in FIG. 17. In this raised sampling position, the through hole 1518 in the stem 1510 is in fluid communication with the sample line 1522 through which the sample flow 31 travels between the sample inlet and outlet ports 1502 and 1504. Accordingly, the flow of carrier solvent is temporarily interrupted and a small sampling of the peak traveling through the sample line 1522 is diverted from the sample line, through the through hole 1518 to the flow outlet port 1508, and into the carrier line at the location where the carrier solvent flow was interrupted. The sampling then flows to the mass spectrometer 16 (FIG. 3) for analysis.

As the peak is moving past the through hole 1518 at a selected time, as determined by the computer controller 18, the stem 1510 is switched back to the lowered position (FIG. 16). The solenoids 1410 are activated, thereby immediately moving the stem 1510 axially to the lowered position, so the only part of the sample flow 31 received by the mass spectrometer 16 for analysis is the sampling of the peak. When the stem 1510 is returned to the lowered position, the flow of the carrier solvent to the mass spectrometer 16 is resumed. Therefore, the mass spectrometer 16 receives a continuous flow of fluid, and the samplings are effectively inserted as segments of that continuous flow when the microsample valve 38 is activated.

The axial movement of the stem 1510 between the lowered position and the raised sampling position allows for an extremely fast switching between positions, thereby providing for small yet highly accurate samplings of the selected portion of the sample flow. In the illustrated embodiment, the microsample valve 28 is configured to be switched from the normal lowered position, to the raised sampling position and back to the normal lowered position within a time period of approximately 15 to 100 milliseconds. In one embodiment the time period is less than 20 milliseconds, so as to divert sample volumes as small as approximately 2 pico liters or less to the mass spectrometer 16. In an alternate embodiment, the microsample valve 28 is configured to be movable from the normal lowered position, to the raised sampling position and back to the normal lowered position in one second or less. This extremely fast switching also minimizes the chance of cross-contamination within the valve body between samplings of a plurality of peaks within the sample flow.

The microsample valve 38 is designed and constructed so the flow paths through the valve body 1408 and the stem 1510 provide virtually no dead space or unswept volumes that could cause cross-contamination between different samples flowing through tote microsample valve.

Accordingly, the microsample valve 38 allows for very accurate results in the purification process. The microsample valve 38 is also configured to quickly take the small sample portions from the sample flow, thereby minimizing the pressure drop in the sample flow across the microsample valve 38. In the illustrated embodiment, the pressure drop across the microsample valve is less than approximately 50 psi.

As best illustrated in FIG. 3, the sample flow 31 in each channel 14 moves from the microsample valve 38 to a pressure relief valve assembly 41 that controls the pressure within the flow downstream of the microsample valve. In the illustrated embodiment, the pressure relief valve assembly 41 has the same construction as the back pressure regulator assembly 55 discussed above, except that the heaters are not provided on the back pressure regulator valve. In alternate embodiments, the heaters can be used if needed as a result of ice formation or larger pressure drops experienced in the system. In other alternate embodiments, other back pressure regulators can be used, provided they are durable enough and provide sufficient pressure control for the purification valve.

The use of the pressure relief valve 41 allows the flow volume to the analyzer to be very small because of either use of a small bore capillary to the analyzer or an active back pressure regulator. Accordingly, the pressure differential is reduced and the flow volume to the mass spectrometer 16 is reduced.

The sample flow 31 exits the pressure relief valve assembly 41 and flows to a flow directing valve, referred to as a fraction collection valve 40. Each fraction collection valve 40 has one inlet port 42, two outlet ports 44 and 46, and a waste port 47. Each fraction collection valve 40 is also operatively coupled to the computer controller 18. When a portion of the sample flow 31 containing a peak enters the fraction collection valve 40 through the inlet port 42, as identified by the computer controller 18, the computer controller activates the fraction collection valve to control whether the peak in the sample flow is directed out of the first outlet port 44 or the second outlet port 46.

If the mass spectrometer 16 determines that the peak is the target compound, the computer controller 18 activates the fraction collection valve 40, so the fraction collection valve moves to a first position. In this position, the sample portion containing the peak is directed out of the fraction collection valve 40 through the first outlet valve 44. The sample portion is directed to a fraction collector assembly 43 and is collected directly into a predetermined location in a selected well of the first receiving microtiter plate 22.

When a portion of a sample flow containing a peak passes through the fraction collection valve 40, and that peak is a crude rather than the target compound, the fraction collection valve is switched to a second position to direct a portion of the sample flow through the second outlet port 46. This portion of the sample flow 31 exits the second outlet port 46, passes through the fraction collection assembly 43 and is collected directly into a selected well of the second receiving microtiter plate 24. When a portion of the sample flow 31 passes through the fraction collection valve and that portion does not contain any peaks, the sample flow passes through the waste outlet 47 and is carried to a waste receptacle 52.

The purification system 10 of the exemplary embodiment allows the purified samples to be automatically dispensed into selected wells 2024 of the receiving microtiter plate 22 or 24. Each purified portion of the sample is dispensed into a well 2024 having the same relative location in the receiving microtiter plate 22 or 24 as the well in the supplying microtiter plate 20 from which the sample was initially drawn to begin the purification run. As an example, referring to FIG. 25, the supplying microtiter plate 20 and each receiving microtiter plate 22 and 24 have a rectangular array of ninety-six wells 2024. Each well 2024 has a well address defined by its position relative to the rows (A–H) and columns (1–12) the array of wells. Accordingly, the well address of the well 2024 in the upper left corner of each plate as shown in FIG. 25 has an address of A1, and the well in the lower right corner has an address of H12.

Information about each sample in each well 2024 of the supplying microtiter plate 20 is known prior to the purification run. When the sample from, as an example, well A1 is drawn out of the supplying microtiter plate 20 and run through the purification system 10, the purified portion of the sample containing the target compound is deposited directly into the corresponding well A1 of the target receiving microtiter plate 22. The purified reaction by-products from that same sample are deposited directly into well A1 of the by-product receiving microtiter plate 24. Therefore, the purified target compound is deposited directly into a well having a one-to-one corresponding well address as the original sample well. Similarly, the reaction by-products are deposited directly into a well having a corresponding one-to-one well address and the second receiving microtiter plate.

This one-to-one mapping of wells 2024 and direct depositing of the target compounds into a selected well of a receiving microtiter plate 22 or 24 allows for easy tracking of information regarding the samples, the purified targets, and the purified reaction by-products. The one-to-one mapping and direct depositing avoids further processing and formatting before the purified target compounds are put into microtiter plates. Accordingly, the efficiency of the purification process is increased and the time and cost requirements are decreased. In addition, receiving microtiter plate 22 or 24 is labeled with, as an example, a bar code so information about the purified components in each receiving microtiter plate is easy to track and maintain.

This purification system 10 of the illustrated embodiment results in the collection of purified compounds having an 85% purity or better. It is preferred, of course, to provide samples having purity as close to 100% pure as possible. Upon collection of the purified target compounds in the receiving microtiter plate 22, these purified target compounds are ready for a screening process or other selected process.

Figure 19:
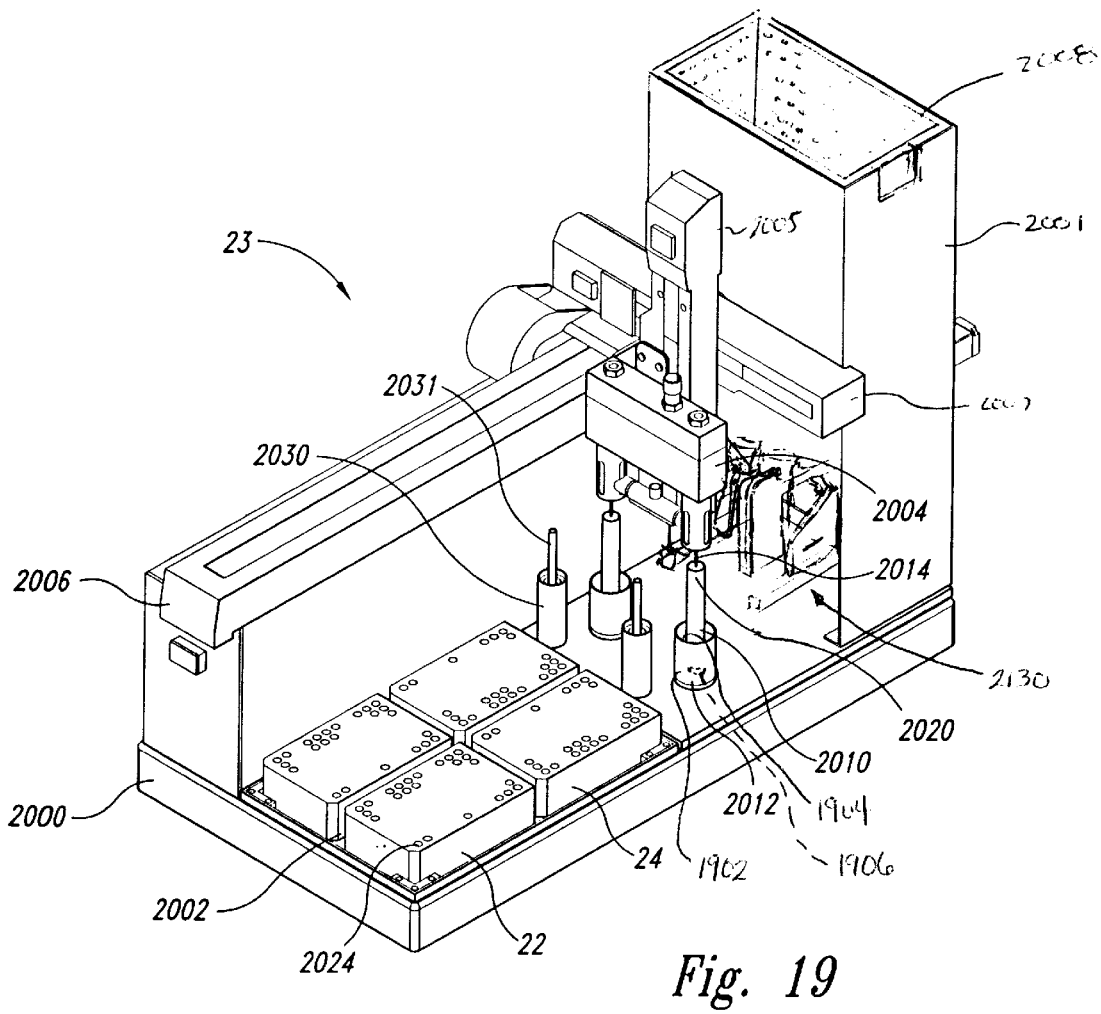
FIG. 19 is an isometric view of an automated fraction collection assembly of the purification system of FIG. 3 in accordance with one embodiment of the invention, the fraction collection assembly shown in a chamber pickup position.
Figure 20:
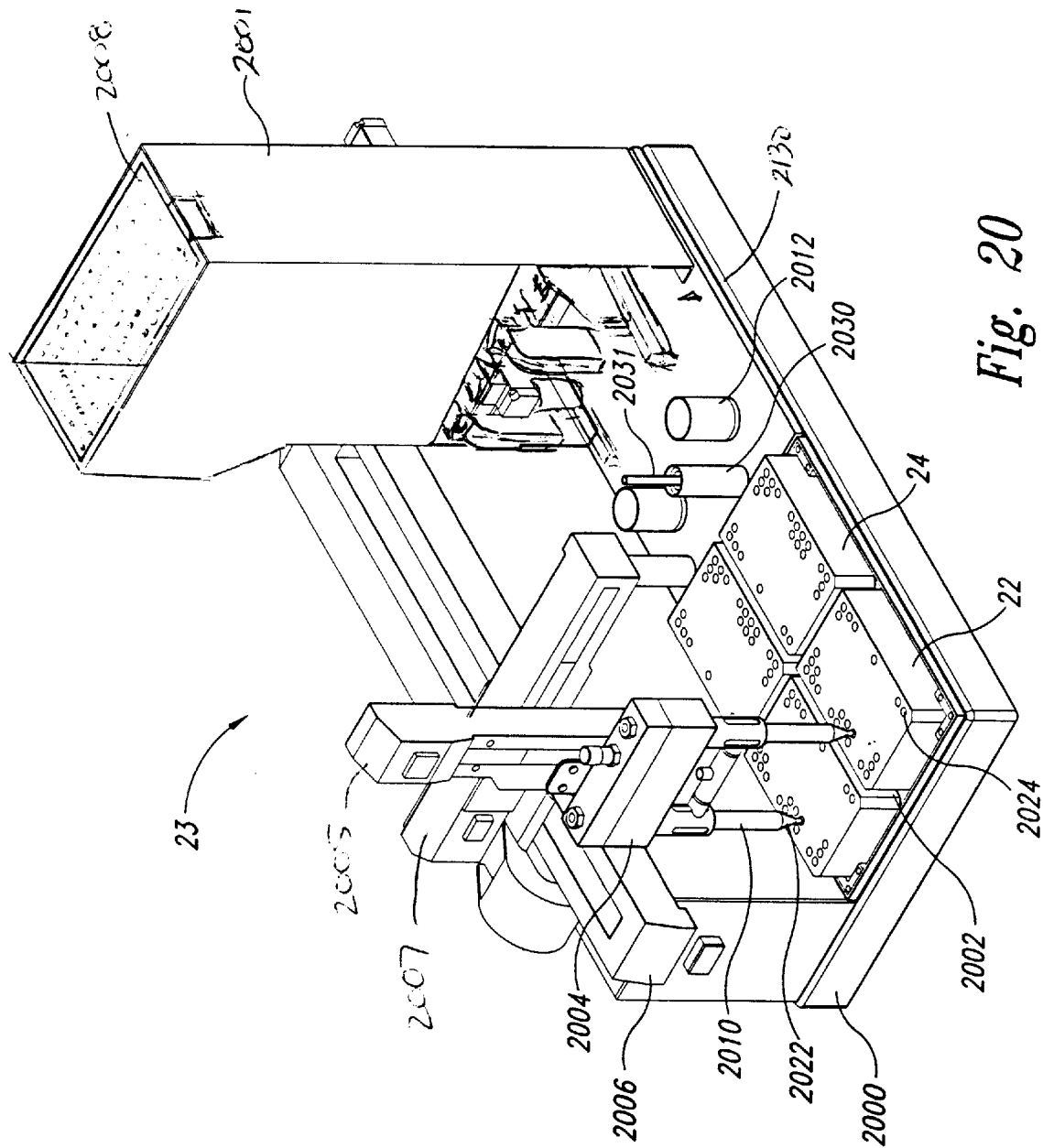
FIG. 20 is an isometric view of the fraction collection assembly of FIG. 19 shown in a collection position.

As best seen in FIGS. 19 and 20, the fraction collector assembly 43 includes a frame 2000 and expansion chamber dispensing assembly 2001 at one end of the frame. A docking station 2002 is supported at the other end of the frame and is positioned to removably receive the receiving microtiter plates 22 and 24. The docking station 2002 includes an array of indicators coupled to the computer controller and positioned to prompt the operator where to place the receiving microtiter plates 22 or 24 on the docking station. In an alternate embodiment, sensors are positioned to detect the location of each receiving microtiter plate 22 or 24 when it is placed on the docking station 2002. The fraction collector assembly 43 also includes a dispensing head 2004 that travels along rails 2005, 2006 and 2007 mounted to the frame 2000 for movement along three axes of movement (X, Y and Z) relative to the frame between several operating positions. Accordingly, the dispensing head 2004 can move fore/aft in the Z-axis along one rail 2006, left/right in the X-axis along another rail 2007, and up/down in the Y-axis along the third rail 2005. This 3-axis movement allows for accurate positioning of the dispensing head 2004 during the fraction collection process, as discussed below.

Figure 21:
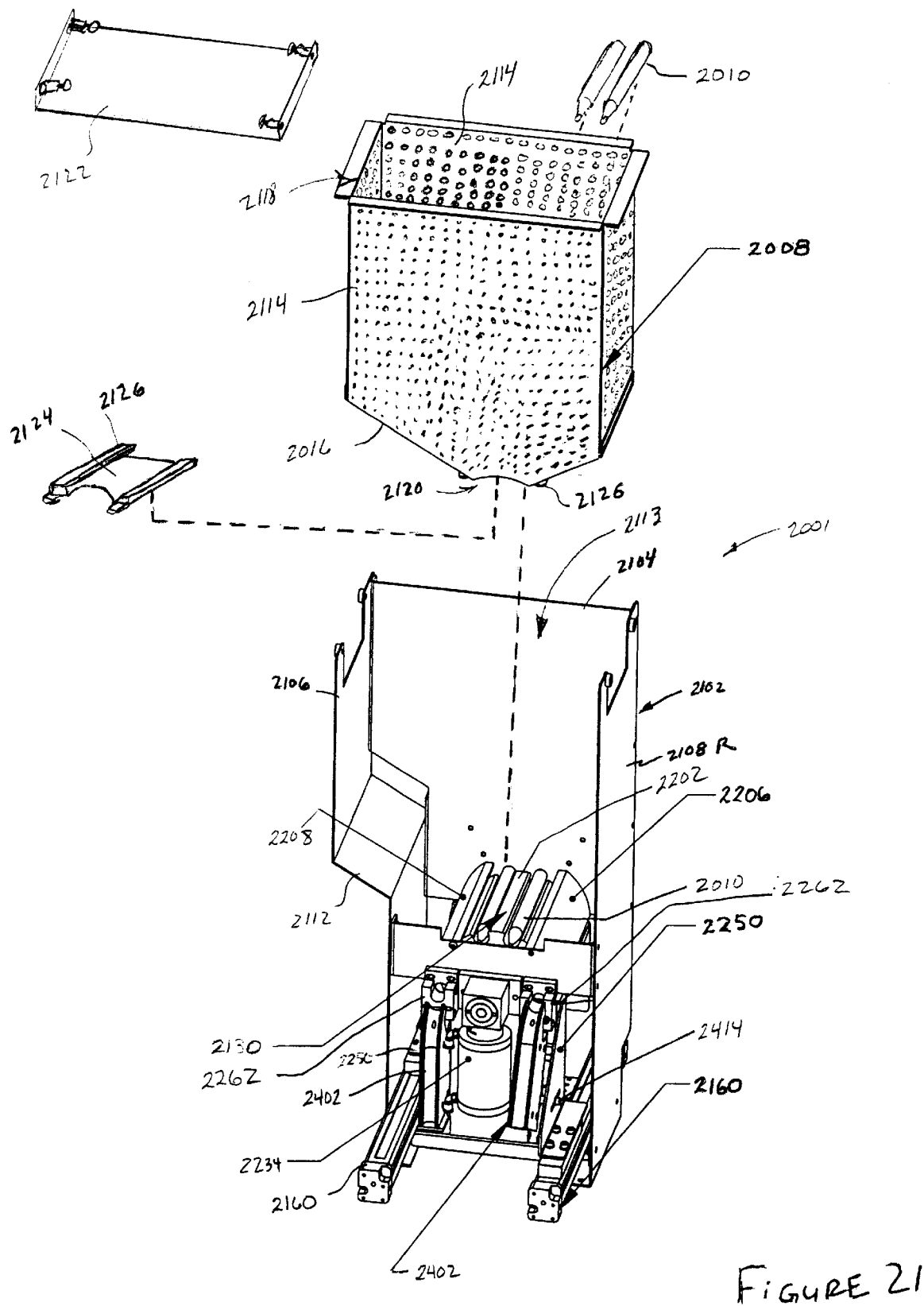
FIG. 21 is an enlarged partially exploded front isometric view of a dispenser assembly and hopper of the fraction collection assembly of FIG. 19 shown removed from the frame for purposes of clarity.

As seen in FIG. 21, the dispensing assembly 2001 includes a housing 2102 formed by a back wall 2104, left and right sidewalls 2106 and 2108. The right sidewall 2108 is a straight vertical wall and the left sidewall 2106 is contoured with a middle angled support portion 2112. Accordingly, the back wall 2104 and the left and right sidewalls 2106 and 2108 define an asymmetric receiving area 2113. The asymmetric receiving area 2113 removably retains an asymmetric hopper 2008 that contains clean disposable or reusable expansion chambers 2010. When the hopper 2008 is in the receiving area 2113, a lower left panel 2016 of the hopper is positioned on the left sidewall's angled support panel 2012. Accordingly, the hopper 2008 has a corresponding asymmetric shape as the receiving area 2113.

The hopper 2008 of the illustrated embodiment is an asymmetric bin formed by a plurality of perforated panels 2114. The perforated panels 2114 of the illustrated embodiment are stainless steel panels, although other materials can be used. The hopper's perforated panel 2114 facing the housing's forward wall 2110 has smaller perforations than those perforations in the panels facing the housing's left and right sidewalls 2106 and 2108 and the rear wall 2104. The smaller perforations in the hopper's front wall are smaller than the tip of the expansion chamber 2010 so the expansion chambers can not extend through the perforations. The larger perforations are larger than the tip of the expansion chambers 2010 but smaller than the open rear ends of the expansion chambers. The expansion chambers 2010 are, thus, installed in the hopper 2008 with the tips facing forwardly toward the panel with the smaller perforations. Accordingly, the smaller perforations in the hopper's front wall provide directional orientation for installation of the expansion chambers 2010. This directional orientation assures easy identification and proper alignment of the expansion chambers 2010 within the hopper 2008. The asymmetric configuration of the hopper 2008 also provides for easy alignment and accuracy of installation of the hopper within the housing 2102 for proper set up of the dispensing assembly 2001 prior to a purification run.

The hopper 2008 has an open top 2118 through which the expansion chambers 2010 can be loaded. The bottom of the hopper 2008 has a dispensing aperture 2120 through which the expansion chambers 2110 are removed during a dispensing operation, as discussed below. A removable top cover 2122 is attachable to the hopper 2008 to cover the open top 2118, and a bottom cover 2124 is slideably attachable to the hopper to close the dispensing aperture 2120. In one embodiment, the top cover 2122 is not installed on the hopper 2008 when the hopper is installed in the housing. The bottom cover 2124 has slide portions 2126 that slideably receive rails 2128 on the hopper 2008 adjacent to the dispensing aperture 2120 so as to retain the bottom cover in a closed position on the hopper 2008.

In the illustrated embodiment, expansion chambers 2010 can be loaded into the hopper 2008 when the bottom cover 2124 is covering the dispensing aperture 2120. The top cover 2122 can then be attached to close the top opening 2118 so as to fully enclose the expansion chambers 2010 within the hopper 2008. If the expansion chambers 2010 contained within the hopper 2008 are not clean or need processing prior to use in the purification run, the hopper with its top and bottom covers 2122 and 2124 can be loaded as a unit into a washing device so as to thoroughly clean the expansion chambers 2120 in preparation for a purification run. The hopper 2008 containing the clean expansion chambers 2010 can then be loaded as a unit directly into the dispensing assembly 2001. The bottom cover 2124 is then removed so the clean expansion chambers 2010 can be dispensed during the purification process.

Figure 22:
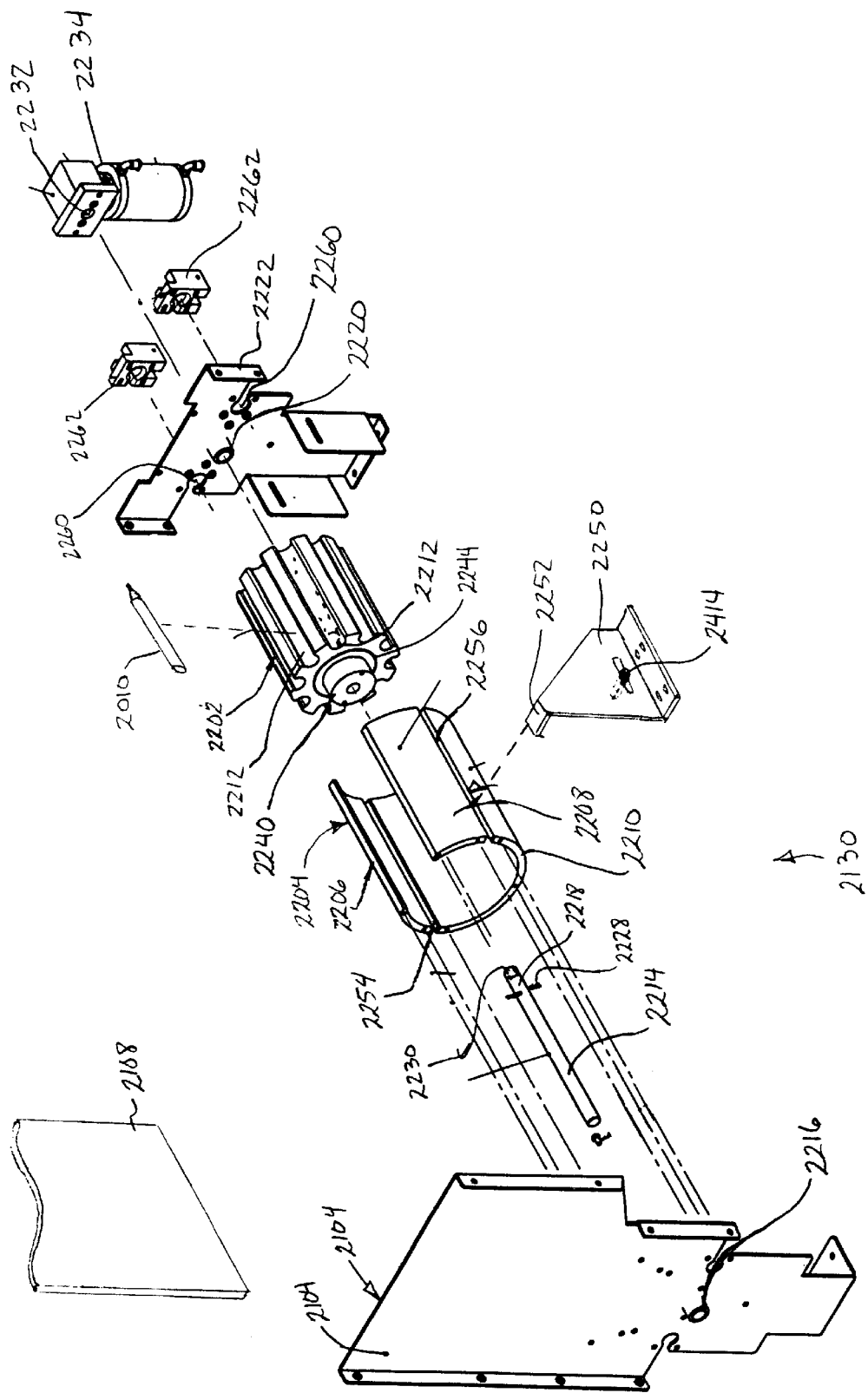
FIG. 22 is an enlarged partially exploded rear isometric view of the drum assembly of FIG. 21.

When the hopper 2008 and expansion chambers 2010 are positioned in the housing's receiving area 2113, the dispensing aperture 2120 is directly above a dispensing drum assembly 2130. As best seen in FIGS. 21 and 22, the drum assembly 2130 includes a horizontally oriented drum 2202 rotatably contained within a drum guide 2204. The drum guide 2204 has separate left, right and bottom guide portions 2206, 2208 and 2210, respectively. The drum 2202 has a plurality of channels 2212 formed along the drum's outer surface parallel with the drum's longitudinal axis. The channels 2212 are arcuate channels shaped to removably receive the expansion chambers 2010 dispensed from the hopper 2008, (FIG. 21). In the illustrated embodiment the drum 2202 has ten channels 2212 formed around it's periphery, although a drum with greater or fewer channels can be used as needed for, as an example, if different size expansion chambers 2010 are to be used.

The drum guide's left and right guide portions 2206 and 2208 have upper edges spaced apart from each other so as to provide an upper opening in the drum guide 2204 for access to the channels 2212 in the drum 2202. The expansion chambers 2010 are dispensed from the hopper 2008 (FIG. 21) into the drum's channels 2212 that are adjacent to the upper opening in the drum guide. The drum guide 2204 extends around the remaining portion of the drum 2202 so as to retain the expansion chambers 2010 within the respective channels 2212 as the drum rotates within the drum guide. Accordingly, the expansion chambers 2010 are loaded into the drum 2202 from the top side, and the drum rotates within the drum guide 2204 to position empty channels 2212 adjacent to the drum guide's opening to receive another clean expansion chamber.

The drum 2202 is mounted on a drive shaft 2214 that rotatably mounts at it's rear end to a bearing 2216 retained in the rear wall 2104 of the housing 2102. A forward portion 2218 of the drive shaft 2214 is rotatably supported in a bearing 2220 in a front mounting plate 2222 to which the housing's front wall 2110 is connected. Accordingly, the drum 2202 is suspended horizontally for rotation relative to the hopper 2008.

Figure 23:
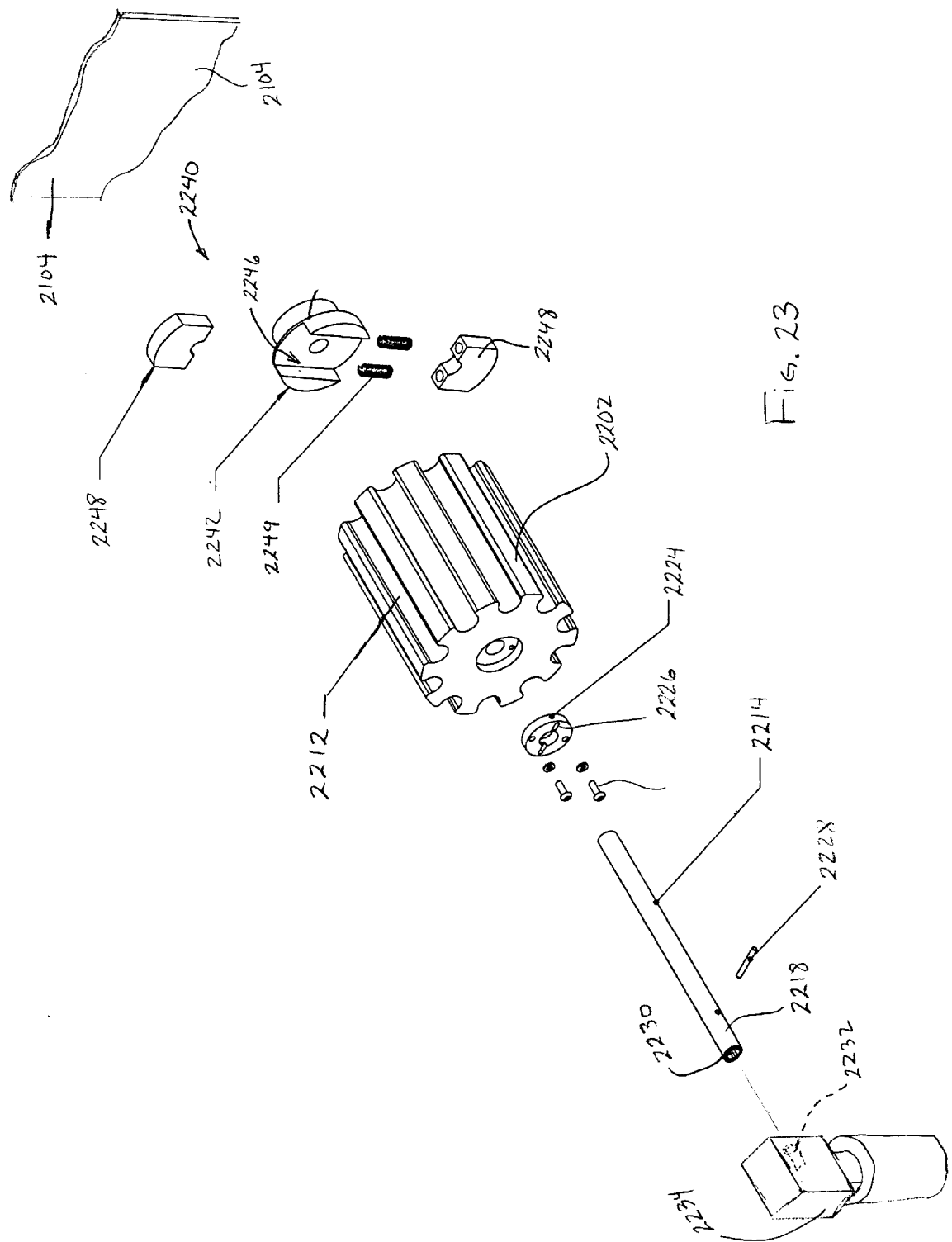
FIG. 23 is an enlarged isometric view of a chamber feed and brake assembly of the drum assembly of FIG. 22.

As best seen in FIG. 23, the drum 2202 has a hub index 2224 securely mounted to the drum's front end. The forward portion 2218 of the drive shaft 2214 extends through the hub index 2224. The hub index 2224 has an elongated slot 2228 that securely receives an index pin 2228 mounted to the drive shaft's forward portion 2218. Accordingly, rotational forced from the drive shaft 2214 are transmitted to the drum 2202 via the index pin 2228 and the hub index 2224 for simultaneous rotation of the drum.

The drive shaft 2214 is rotatably driven by a drum actuator 2234 securely mounted to the front mounting plate 2222 (FIG. 22). The drum actuator 2234 has a shaft 2232 that extends into a keyhole 2230 in the drive shaft's forward portion 2218. In the illustrated embodiment, the keyhole 2230 has a non-circular cross-sectional shape, such as a square or a hexagonal shape, that receives the similarly shaped shaft 2232 of the drum actuator 2234. The drum actuator 2234 is coupled to and controlled by the purification system's computer controller 18 so as to accurately control rotation of the drum 2202 for selected loading and dispensing of the expansion chambers 2010.

As best seen in FIGS. 22 and 23, a drum brake 2240 is connected to the back end portion of the drum 2202. The brake 2240 includes a break hub 2242 securely mounted to the housing's back wall 2104 (FIG. 22). The brake hub 2242 extends into a cylindrical break recess 2244 formed in the drum's back end portion. As best seen in FIG. 23, the brake hub 2242 has an enlarged channel 2246 that slidably receives a pair of brake pads 2248. The brake pads 2248 are biased radially outwardly by a pair of springs 2249 to frictionally engage the drum 2202 within the brake recess 2244. The springs 2249 are selected to provide sufficient biasing force for frictional engagement between the brake pads 2248 and drum 2202 to allow for rotation of the drum 2202 when the drum actuator 2234 is activated. The frictional engagement, however, is sufficient to quickly stop rotation of the drum 2202 when rotation of the drum actuator 2234 stops, thereby preventing drum-overdrift relative to the hopper's dispensing aperture 2120 (FIG. 21). Accurately controlling drum position and preventing drum-overdrift allows for accurate alignment of the drum's channels 2212 relative to the hopper 2008 for fast and accurate positioning of the expansion chambers 2010 into the channels.

After an expansion chamber 2010 has been loaded into a selected channel 2212 in the drum 2202, the drum actuator 2234 rotates the drum to move the loaded expansion chamber into a dispensing position. As seen in FIG. 21, dispenser brackets 2250 are slidably positioned adjacent to the left and right sides of the drum 2202. Each dispenser bracket 2250 is positioned to push the expansion chamber 2010 axially out of its respective channel 2212 and, thereby dispensing the expansion chamber from the drum 2202. Each dispenser bracket 2250 engages the expansion chamber 2010 with a generally horizontally oriented dispenser tab 2252. The dispenser tab 2252 is positioned to slide through a raceway 2254 formed in the respective left or right side of the drum guide 2204. In the illustrated embodiment, the drum guide 2204 has a left raceway 2254 formed by a space between the left guide portion 2206 and the bottom guide portion 2210. A right raceway 2256 is formed by a space provided between the right guide portion 2208 and the bottom guide portion 2210.

The dispenser tabs 2252 are sized to extend through the respective left or right raceway 2254 or 2256 and partially into the channel 2212 adjacent to that raceway. The dispenser tabs 2252 engage the large open end of the expansion chamber 2010 contained in the channel 2212 positioned adjacent to the respective left or right raceway 2254 or 2256. When the dispensing assembly is ready to dispense an expansion chamber 2010, the dispenser bracket 2250 is moved forwardly so the dispenser tab 2252 slides axially along the raceway 2254 or 2256 and through the channel 2212, thereby pushing the expansion chamber 2010 axially out of the channel. In the illustrated embodiment, the dispenser brackets 2250 can be moved simultaneously or independently to dispense two expansion chambers 2010 from the drum assembly 2130 as needed during the selected purification run.

Figure 24:
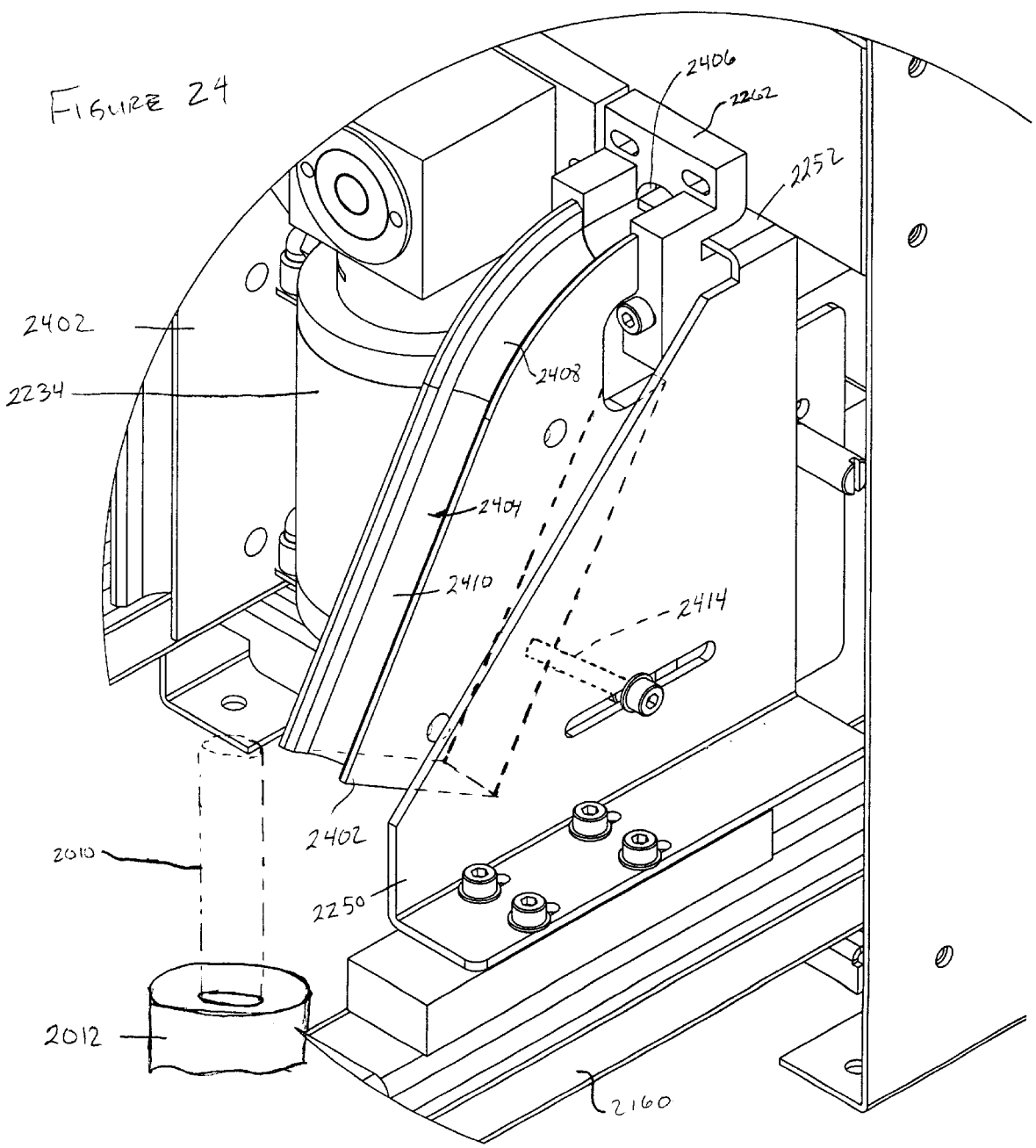
FIG. 24 is an enlarged partial isometric view of the distribution assembly of FIG. 21 with a right alignment guide shown in a forward dispensing position and a left alignment guide shown in a retracted position.
Figure 26:
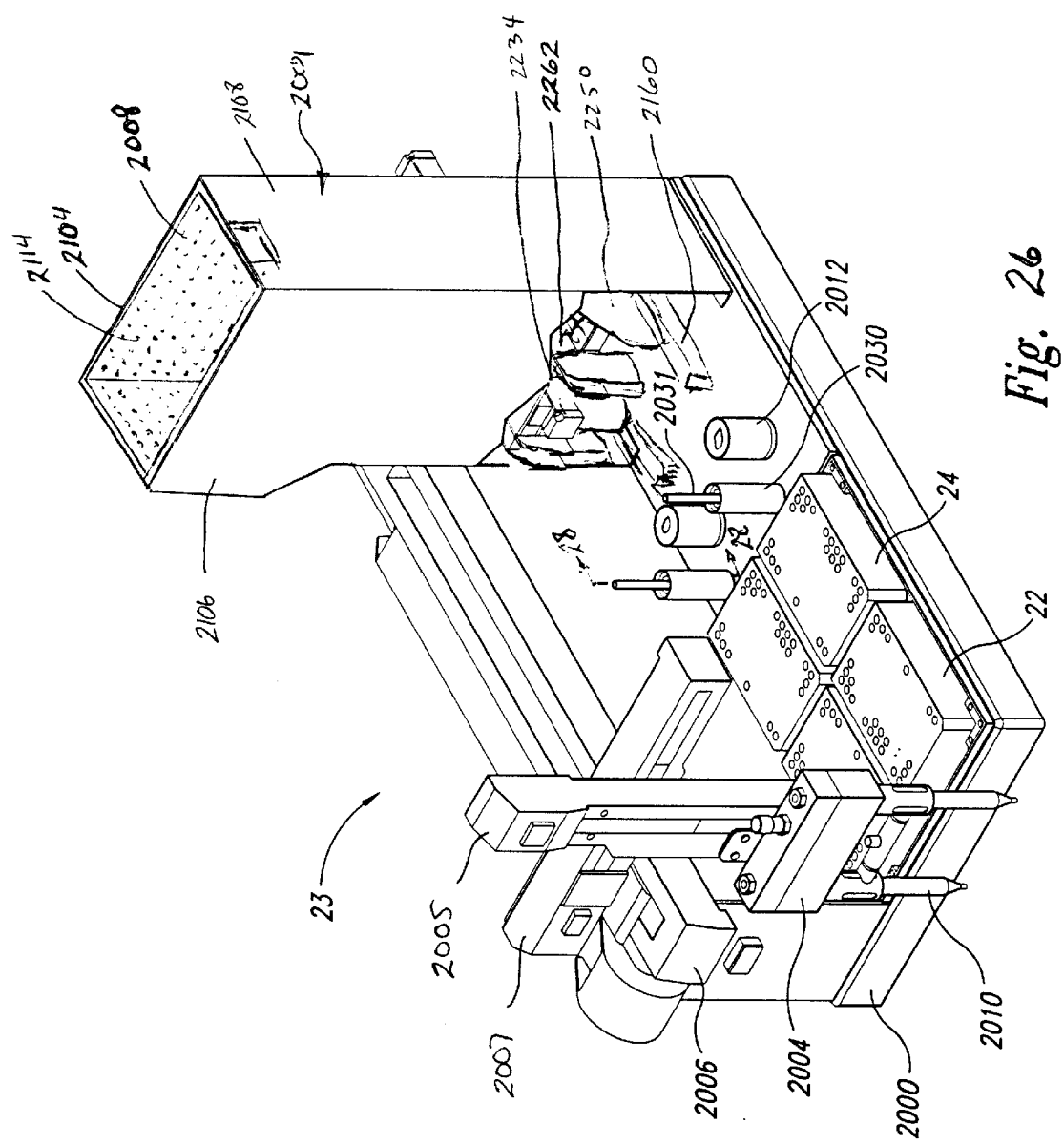
FIG. 26 is an isometric view of the fraction collection assembly of FIG. 19 shown in a chamber drop-off position.
Figure 27:
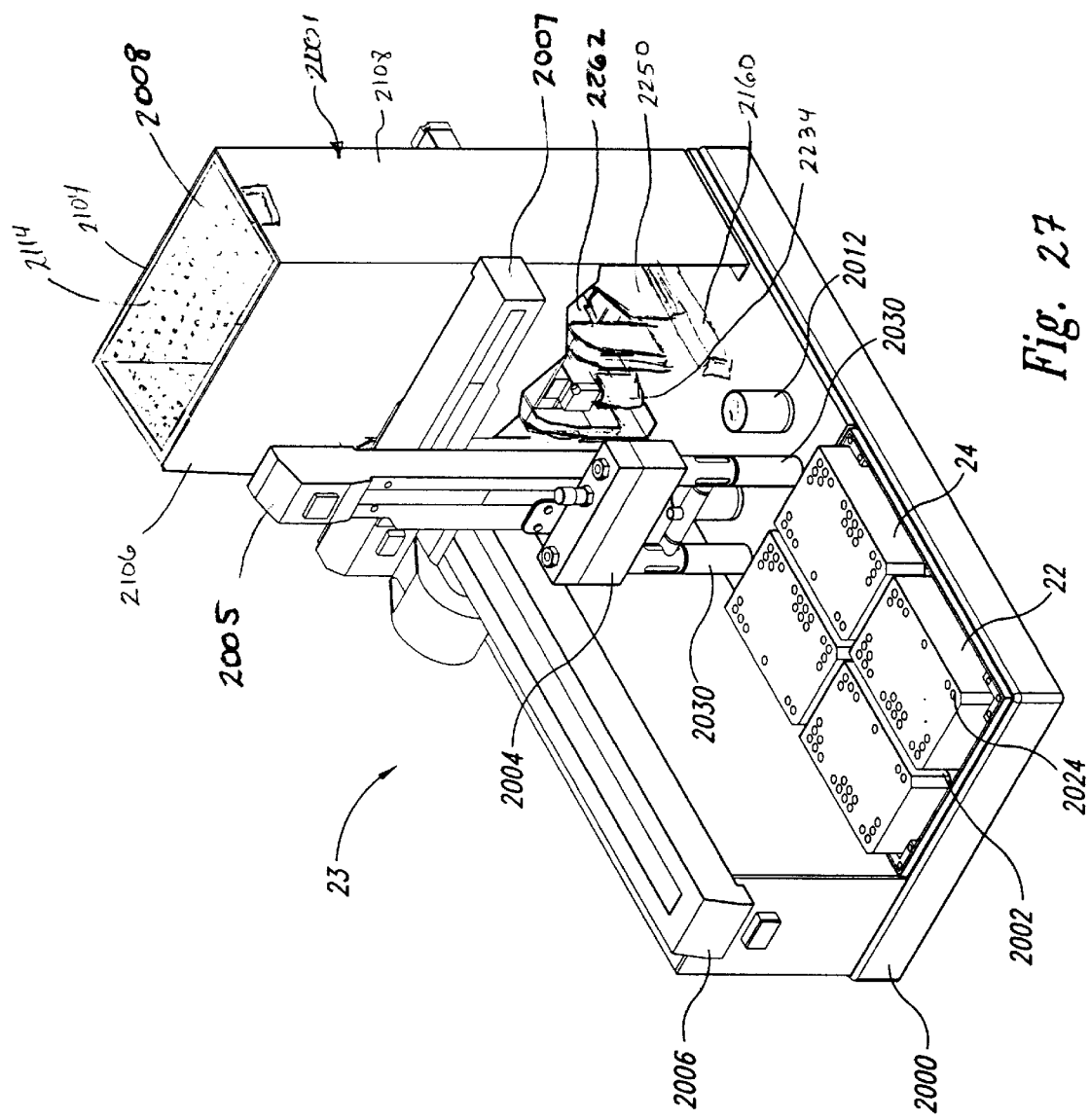
FIG. 27 is an isometric view of the fraction collection assembly of FIG. 19 shown in a rinse position.
Figure 2B:
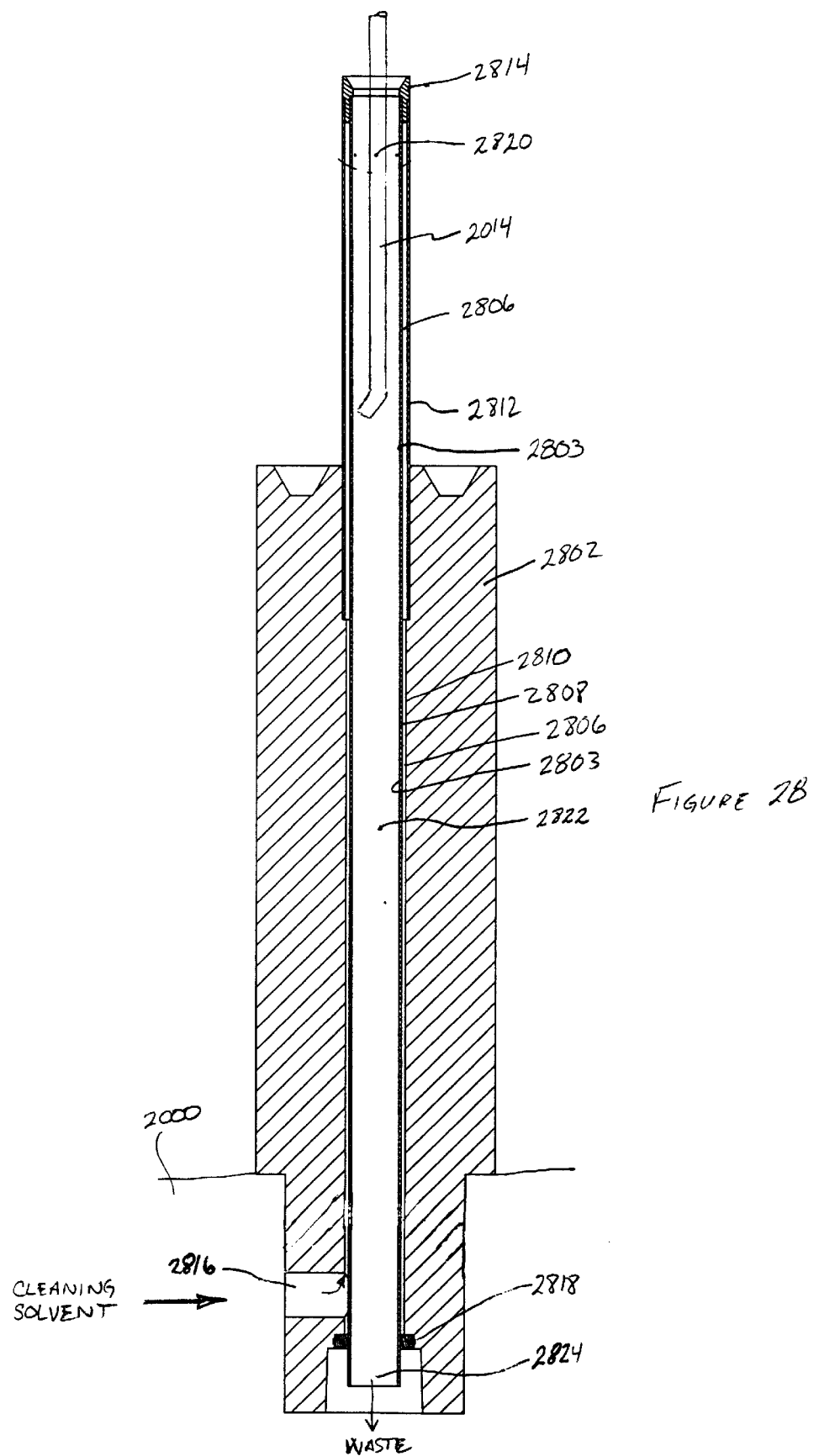

As best seen in FIGS. 21 and 24, each of the left and right dispenser brackets 2250 are slideably mounted on rails 2160 for movement between a rearward position and a forward position. The right dispenser bracket 2250 is shown in FIG. 21 in the forward position, and the left dispenser bracket is shown in the rearward position. Each dispenser bracket 2250 is movable linearly along the rail 2160 by an actuator coupled to the computer controller 18 of the purification system 10. Accordingly, the computer controller 18 controls the timing for movement of the dispenser brackets 2250 along the respective rails 2160, thereby controlling the dispensing of the expansion chambers 2010. The actuators for each of the left and right dispenser brackets 2250 are independently controlled so the dispenser brackets can be moved simultaneously or at separate times for dispensing of the expansion chambers 2010.

As each dispenser bracket 2250 moves from the rearward position toward the forward position, the dispenser tab 2252 slides the expansion chamber 2010 forwardly along the drum's channel 2212. The expansion chamber 2010 slides tip first through an aperture 2260 in the front mounting plate 2222 and through a respective left or right alignment mount 2262. Each alignment mount 2262 is coaxially aligned with the channel 2212 from which the expansion chamber 2010 is dispensed.

Once the expansion chamber 2010 has been pushed out of its channel 2212 in the drum 2202, the dispenser bracket 2250 is returned to its rearward position. The drum actuator 2234 rotates the drum 2202 to move another clean expansion chamber 2010 into alignment with the respective left or right raceway 2254. In the illustrated embodiment, the dispensing assembly 2001 can dispense two expansion chambers 2010 simultaneously from the drum 2202. Accordingly, the drum actuator 2234 is indexed to move the drum 2202 two positions relative to the raceways 2254 and 2256 and the dispenser brackets 2250 upon each activation of the actuator. This two position movement results in a timing and pattern that always provides an expansion chamber in the channel 2212 in alignment with both dispenser brackets 2250. While the illustrated embodiment provides indexing of the drum by two positions, other indexing configurations can be used by controlling the drum actuator 2234 for movement of the drum 2202.

As best seen in FIGS. 21 and 24, the dispensing assembly includes left and right chamber guides 2402 pivotally mounted adjacent to the alignment mounts 2262 on the front mounting plate 2222. The chamber guides 2402 are pivotally movable between a forward, dispensing position, as shown in FIG. 24, and a rearward, stowed position, as shown with the left chamber guide in FIG. 21. Each chamber guide 2402 has a guide channel 2404 adapted to receive the expansion chamber 2010 as the expansion chamber is pushed through an alignment aperture 2406 in the alignment mount 2262. The upper portion 2408 of the guide channel 2404 has a convex shape and it is positioned at its top end below the alignment aperture 2406 in the alignment mount 2262. The guide channel's upper portion 2408 is integrally connected at its bottom end to a straight slide portion 2410. Accordingly, when the expansion chamber 2010 is pushed through the alignment aperture 2406, it slides over the convex upper portion 2408 of the guide channel 2404 and down the straight slide portion 2410. When the chamber guide 2402 is in the forward, dispensing position, the straight slide portion 2410 is aimed to direct the expansion chamber 2010 to slide into the pickup station 2012, so the expansion chamber is held in a vertical orientation with its tip pointing downwardly.

The chamber guide 2402 is moved from the rearward, stowed position to the forward, dispensing position by a displacement pin 2414 projecting inwardly from the respective left or right dispenser bracket 2250. As the dispenser bracket 2250 moves from the rearward position to the forward position, as shown in FIG. 24, the displacement pin 2414 engages the back side of the chamber guide 2402 and pivots the chamber guide forwardly to the forward, dispensing position. The dispenser guide 2402 is biased by a spring toward the rearward stowed position.

In the illustrated embodiment, the displacement pin 2414 is positioned along an elongated slot 2416 in the dispenser bracket 2250 to provide adjustability for the displacement pin's position relative to the chamber guide 2402. Such adjustment is provided to allow for accurate positioning of the chamber guide 2402 to properly aim the straight slide portion 2410 when the chamber guide is in the forward, dispensing position, so the expansion chambers 2010 consistently land in the pickup station 2012.

As the dispenser bracket 2250 and displacement pin 2414 are moving forwardly, the dispenser tab 2252 is simultaneously pushing the expansion chamber 2010 forwardly. The alignment mounts 2406 are positioned to hold the expansion chambers 2010 substantially horizontal as they are pushed through the alignment apertures 2406 until the expansion chamber's open top end 2020 is pushed through the alignment aperture 2406. Once the expansion chamber 2010 moves fully out of the alignment aperture 2406, the expansion chamber drops into the guide channel 2404 and slides along the channel and into the pickup station 2012. When the dispenser bracket 2250 and displacement pin 2414 returns to the rearward position, the alignment guide 2402 also returns to the rearward, stowed position spaced apart from the pickup station 2012 and the dispensed expansion chamber 2010.

As best seen in FIG. 19, the pickup stations 2012 holds the expansion chambers 2010 in a substantially vertical orientation with the open top end 2020 of the expansion chamber facing upwardly. Each pickup station 2012 has a cylindrical housing 1902 with a cylindrical aperture 1904 that removably receives the expansion chambers 2010 from the respective left or right chamber guide 2402. The cylindrical housing 1902 has a biasing member 1906, such as a sprig, in the cylindrical aperture 1904 so as to support the tip end of expansion chamber 2010 when loaded into the pickup station 2012. The biasing member 1906 allows the expansion chamber 2010 to move axially within the pickup station 2012 if a downward force is exerted on the expansion chamber 2010. Accordingly, if the expansion chamber 2010 is axially misaligned with the dispensing head 2004 as the dispensing head attempts to pick up the expansion chamber, the biasing member 1906 absorbs some of the force and protects the misaligned expansion chamber 2010 from being damaged.

In one embodiment, the pickup station 2012 has optical sensors in the housing's cylindrical aperture 1904 and coupled to the system's computer controller 18. The optical sensors detect whether an expansion chamber has been properly dispensed into the pickup station 2012. If the optical sensors do not properly detect an expansion chamber 2010 as the dispensing head 2004 begins its pickup process, a signal is provided to the system's computer controller and the computer controller stops the pickup motion and generates an error message. The dispensing head 2004 is movable along the rails 2005, 2006 and 2007 to a position over the pickup station 2012 and movable downwardly to pickup the expansion chamber. As the dispensing head 2004 moves downwardly, dispensing needle 2014 on the dispensing head 2004 extend into the expansion chambers 2010 through the chamber's open top end 2020. In the exemplary embodiment, the dispensing head 2004 is positioned so the dispensing needles 2014 are initially coaxially aligned with the expansion chambers 2010 in the pickup station 2012. As the dispensing head 2004 is moved downwardly so the dispensing needles 2014 extend into the expansion chambers 2010, the dispensing head slightly moves along the X-axis or Z-axis, thereby axially misaligning the dispensing needles within the expansion chambers. This axial misalignment of the: dispensing needles 2014 within the expansion chambers 2010, as discussed below, facilitates sample collection through the expansion chambers.

When the dispensing head 2004 moves to the lowered position, the dispensing head extends over the open top end 2020 of the expansion chambers 2010. The dispensing head 2004 grasps the expansion chamber 2010 around the open top end 2020, and lifts it out of the pick-up station 2012. As best seen in FIG. 20, the dispensing head 2004 moves along the rails 2005, 2006, and 2007, and moves the expansion chambers 2010 from the pickup station 2012 to a dispensing position over selected wells 2024 in the receiving microtiter plates 22 and 24. The dispensing head 2004 is coupled to the computer controller 18 that controls the positioning of the expansion chambers 2010 over the wells 2024 so as to correspond to the well locations from which the sample was originally taken in the one-to-one well correspondence, as discussed above. The dispensing head 2004 moves the expansion chambers 2010 downwardly so as to extend at least partially into the selected wells 2024. Once the expansion chamber 2010 is lowered, the sample portion containing either the target or the sample by-product is deposited from the dispensing needle 2014, into the expansion chamber 2010, and into the selected well 2024 in the microtiter plate 22 or 24.

Figure 18:
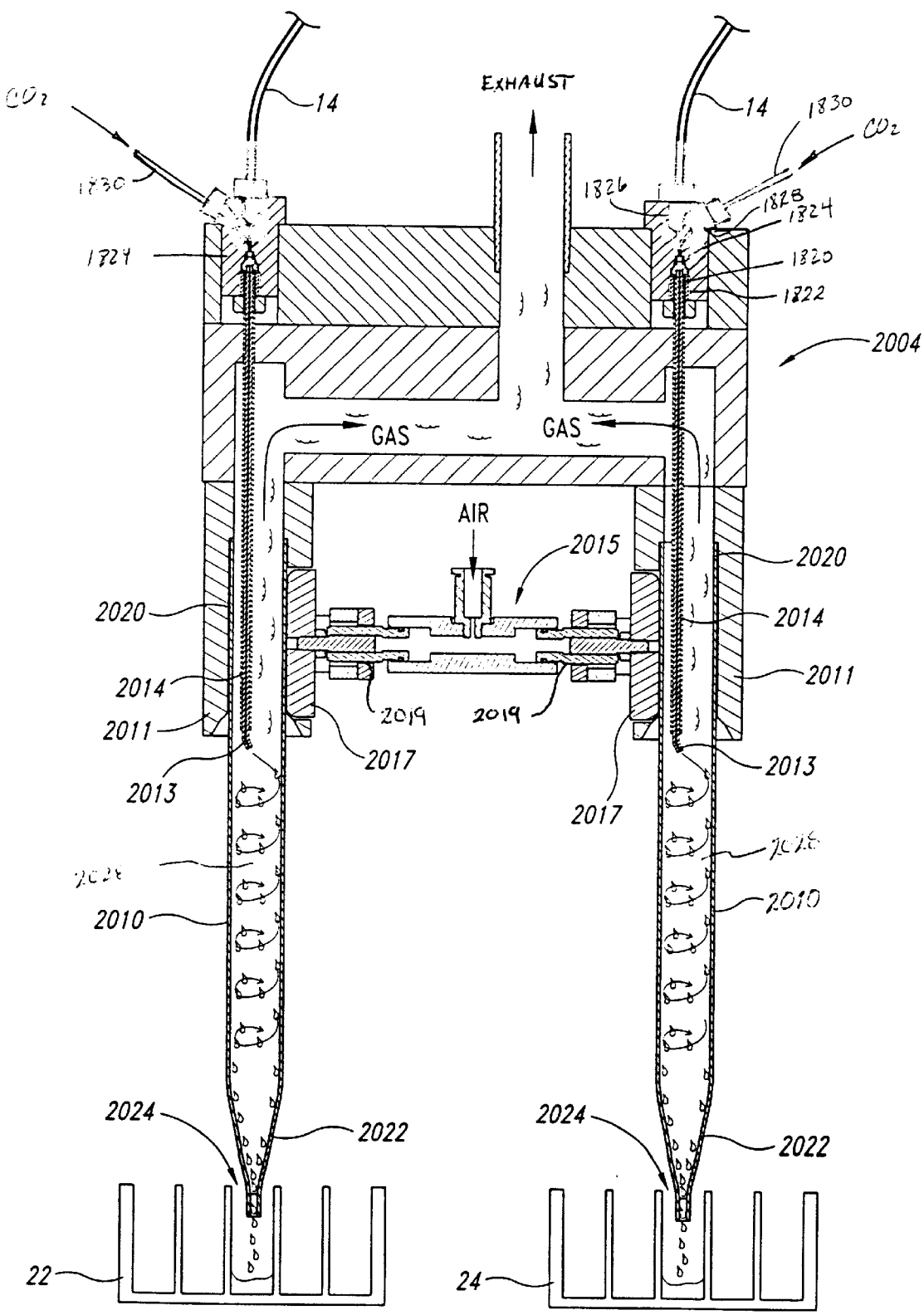
FIG. 18 is an enlarged cross-sectional view of a dispensing head and an expansion chamber from the purification system of FIG. 3, the dispensing head being shown in a dispensing position.

As best seen in FIG. 18, the dispensing head 2004 of the illustrated embodiment releasably holds two expansion chambers 2010 in tubular holding members 2011. A pneumatic gripping assembly 2015 is connected to each tubular holding member 2011 in a position to releasably engage the expansion chambers 2010. The gripping assembly 2015 includes a pair of grippers 2017 connected to pneumatic cylinders 2019. The pneumatic cylinders 2019 move the grippers 2017 relative to the tubular holding member 2011 between holding and released positions. In the holding position, each gripper 2017 presses the expansion chamber 2010 against the tubular holding member 2011, so the expansion chamber is frictionally held in the tubular holding member. In the released position, each gripper 2017 is positioned to allow the respective expansion chamber 2010 to freely move into or out of the tubular holding member 2011.

The expansion chamber 2010 is a tubular member having the open top end 2020 that is releasably engaged by the gripping assembly 2015 of the dispensing head 2004, and a tapered, open bottom end 2022. The open bottom end 2022 is positionable partially within a selected well 2024 of the microtiter plate 22 or 24. The expansion chamber's open top end 2020 is positioned so the dispensing needle 2014 extends therethrough into the expansion chamber's interior area 2028. The dispensing needle 2014 is positioned adjacent to the expansion chamber's sidewall with the needle axially misaligned with the expansion chamber. The distal end 2013 of the dispensing needle 2014 is angled so as to point toward the respective expansion chamber's sidewall.

Each dispensing needle 2014 receives the sample portions through its open top end 1820 that connects to an outlet port 1822 in a coupler 1824. The coupler 1824 has, on its top end, a sample inlet port 1826 coaxially aligned with the outlet port 1822. Accordingly, the coupler 1824 directs the sample portion containing the target or reaction by-product into the dispensing needle 2014 for delivery into the expansion chamber 2010.

The coupler 1824 of the illustrated embodiment also has a secondary inlet port 1828 in fluid communication with the coupler's outlet port 1820. The secondary inlet port 1828 is connected to a small-bore, high pressure line 1830 carrying liquid carbon dioxide, nitrogen, or other selected chilled liquid or gas. The coupler 1824, thus, can selectively direct a flow of the pressurized liquid or gas into the dispensing needle 2014.

In one embodiment, the fraction collection assembly 23 is configured to direct a flow of high pressure liquid carbon dioxide gas through the coupler 1824 and the dispensing needle 2014 before the sample portion is directed through the needle. This flow of high pressure liquid carbon dioxide against sidewalls of the expansion chamber 2010 chills the sidewalls to facilitate collection of the sample portion. As the sample portion is dispensed from the dispensing needle 2014 into the interior area 2028 of the expansion chamber 2010, the sample portion is in an atomized state. The atomized sample portion enters the expansion chamber 2010 through the needle's angled distal end 2013, and the distal end direct the flow toward the expansion chamber's sidewall. The atomized sample portion condenses on the expansion chamber's chilled sidewalls as a liquid, and is directed so the condensed liquid moves along the sidewalls in a downwardly spiral direction.

The condensed, non-atomized liquid sample portion flows out of the open expansion chamber's bottom end 2022 into the selected well 2024 in the microtiter plate 22 or 24. As the atomized sample portion is being dispensed into the expansion chamber 2010, the $CO_2$ vapor exits the expansion chamber through its open top end 2020. In the illustrated embodiment, a vacuum is drawn within the expansion chamber to draw the $CO_2$ vapors out and away from the expansion chamber's open top end 2020, thereby avoiding cross-contamination between channels. After a sample portion has been passed through the dispensing needle, a puff of carbon dioxide or other gas can be passed through the dispensing needle to ensure that there is no residual fluid left in the needle.

As the sample portion is condensed in the expansion chamber 2010, some of the liquid sample portion may remain in the bottom of the expansion chamber because of a capillary action at the narrow open bottom end 2022. At this point, the fraction collection valve dispenses a selected solvent into the expansion chamber to rinse it out and carry any remaining sample into the microtiter plate 22 or 24. After the sample portion has been fully dispensed, the dispensing head 2004 can provide a puff of carbon dioxide or other gas into the expansion chamber 2010. The gas forces the remaining liquid sample out of the expansion chamber 2010 and into the well 2024.

As best seen in FIG. 26, after the sample has been dispensed into the microtiter plate 22 or 24, the dispensing head 2004 moves to a chamber drop-off position so the expansion chambers 2010 are positioned past the edge of the frame 2000. The gripping assembly 2015 of the dispensing head 2004 moves to the released position and the expansion chambers 2010 drop into a suitable waste receptacle. In one embodiment, the expansion chambers 2010 are thrown away. In an alternate embodiment, the expansion chambers 2010 are recycled so as to be reusable. In another embodiment, the used expansion chambers 2010 are collected in receiving hopper substantially identical to the hopper 2008 in the chamber dispensing assembly 2001 discussed above. The receiving hopper with the used expansion chambers 2010 can be taken as a unit and placed into a washing assembly that cleans the expansion chambers. The receiving hopper and clean expansion chambers 2010 can then be loaded directly into the housing 2102 of the dispensing assembly 2001. Accordingly, use of the receiving hopper can save a significant amount of time and manpower in preparing the expansion chambers for use in the fraction collection assembly 23.

After the dispensing head 2004 drops off the expansion chambers, the dispensing head moves to a needle rinse position, illustrated in FIG. 22. In this needle rinse position, the dispensing head 2004 is positioned over a pair of rinse stations 2030. As seen in FIG. 28, each rinse station 2030 includes a substantially cylindrical body 2802 mounted at its bottom end to the frame 2000 of the fraction collection assembly 23. The body 2802 has an elongated aperture 2804 extending vertically along the body's longitudinal axis. An inner wash tube 2803 is positioned within the elongated aperture 2804. The inner wash tube 2806 has an outer diameter smaller than the aperture's inner diameter, such that an annular passageway 2806 is formed between the wash tube and the body.

An outer wash tube 2812 is concentrically disposed around the inner wash tube 2803. The outer wash tube 2812 has an inner diameter greater than the inner wash tube's outer diameter. Accordingly, the annular solvent passageway 2806 extends between the inner and outer wash tubes 2803 and 2812. The inner and outer wash tubes 2803 and 2812 are held in the concentric orientation by a top cap 2814 that provides a top closure to the solvent passageway 2806.

The bottom portion of the body 2802 has a solvent inlet port 2816 coupled to a solvent source and in fluid communication with the solvent passageway 2806. A selected solvent or other cleaning fluid is directed through the solvent inlet 2816 and into the solvent passageway 2806. An O-ring seal 2818 is positioned in the bottom portion of the body 2802 and around the inner wash tube 2803 so as to provide a bottom closure to the solvent passageway 2806. The solvent enters the solvent passageway 2806 and flows upwardly through the passage. The upper end portion of the inner wash tube 2803 has a plurality of holes 2820 that communicate with the solvent passageway 2806. The solvent flowing through the solvent passageway is forced through the holes 2820 into the interior area 2822 of the inner wash tube 2803. The holes 2820 are sized to direct jets of the solvent radially inwardly from the periphery of the interior area 2822.

When the dispensing needle 2014 is lowered into its respective rinse station 2030, the dispensing needle is positioned within the inner wash tube's interior area 2822. The computer controller 18 activates the flow of solvent from the solvent source, and solvent flows into the annular solvent passageway 2806 and through the holes 2820 into the interior area 2822. The jets of cleaning solvent clean or rinse the dispensing needle 2014. In the exemplary embodiment, the cleaning solvent is dispensed through the holes 2820 when the dispensing needle 2014 is moved upwardly out of the inner wash tube 2803. As the dispensing needle 2014 moves upwardly, the jets of cleaning solvent hitting the dispensing needle act as a "fluid squeegee," thereby cleaning the dispensing needle from its top or middle portion to its tip as the dispensing is withdrawn from the inner wash tube 2803.

The cleaning solvent that flows into the inner wash tube's interior area 2822 flows downwardly through the interior area and exits the inner wash tube through an open bottom end 2824. The open bottom end 2824 is coupled to a waste line that carries the used cleaning solvent to a selected receptacle for containing the waste solvent.

After the dispensing needles 2014 are lifted out of the wash stations 2030. The dispensing head 2004 is moved back to the expansion chamber pickup position, illustrated in FIG. 19. New, clean expansion chambers 2010 that have been delivered to the pickup stations 2012 are then picked up by the dispensing head 2004 for dispensing other sample portions into the respective receiving microtiter plates 22 and 24.

The high throughput purification system 10 of the illustrative embodiment allows for relatively fast sample purification as compared to conventional purification processes. A purification run of a selected sample can be accomplished in approximately 6–8 minutes or faster. Therefore, purification of samples contained in a 96 well microtiter plate will take approximately 144–192 minutes. Purification of 4,000 samples generated in a week using sample generation techniques, discussed above, will only take in the range of 250–330.3 hours, as opposed to the 2,000 hours required to purify the 4,000 samples, using conventional purification techniques. Therefore, the high throughput purification system in accordance with the present invention allows for a significant increased speed of purification. This system also provides for collecting the purified samples directly into a microtiter plate in wells having a location address corresponding to the location address of the well in the microtiter plate from which the samples were originally drawn. Thus, the purified compounds are ready to be screened or otherwise processed. The result is a significantly increased capacity for purification that allows for a less expensive purification process.

From the foregoing it will be appreciated that, although specific embodiment of the invention have been described herein for purposes of illustration, various modifications may be made without deviating from the spirit and scope of the invention. Accordingly, the invention is not limited except as by the appended claims.

What is claimed is:

1. A fraction collector assembly useable to collect a purified target portion of a selected sample taken from one of a plurality of supplying wells in a supplying container, the one supplying well having a well-position address for its position in the supplying container, comprising:
   a frame;
   a dispensing head movable relative to the frame along three axes of movement, the dispensing head being configured to dispense the target portion of the selected sample;
   a receiving container having a plurality of receiving wells sized to receive the target portion of the selected sample when the dispensing head is in the dispensing position, each receiving well having a well-position address;
   a docking station releasably retaining the receiving container in a selected position to receive the target portion; and
   a computer controller configured to identify the well-position address for the one supplying well relative to the supplying container, the computer controller being coupled to the dispensing head and configured to control movement of the dispensing head relative to the docking station to dispense the selected target portion directly into a receiving well having a well-position address relative to its position in the receiving container that directly corresponds to the well-position address of the one supplying well relative to the supplying container.

2. The fraction collector assembly of claim 1, target sample portion is provided to the dispensing head in a vaporous state, the fraction collector assembly further comprising a tubular expansion chamber shaped to receive the target portion in a vaporous state and cause the target portion to condense into liquid format for delivery directly to the receiving well.

3. The fraction collector assembly of claim 2, further comprising a pick up station connected to the frame, the pick up station having a holding member that releasably holds the expansion chamber in a selected position for engagement by the dispensing head; and an expansion chamber delivery assembly adjacent to the pick up station, the delivery assembly having delivery member that receives an expansion chamber and delivers it to the pick up station in the selected position.

4. The fraction collector assembly of claim 1 wherein the docking station has an indicator coupled to the computer controller, the indicator is positioned to identify where the receiving container is to be positioned in the docking station.

5. The fraction collector assembly of claim 1 wherein the receiving container is a multiple well microtiter plate.

6. The fraction collector assembly of claim 1 wherein the docking station has a sensor coupled to the computer controller, the sensor is positioned to determine if the receiving container is positioned in the docking station.

7. An automated fraction collector assembly useable to collect sample portions of a selected sample, comprising:
   a frame;
   a dispensing head movably connected to the frame, the dispensing head being configured receive the sample portion and to dispense the sample portion, the selected sample being provided to the dispensing head in a substantially vaporous state;
   a receiving container having a plurality of receiving wells, each well being sized to receive the sample portion of the selected sample;
   an expansion chamber engageable by the dispensing head and being shaped to receive the sample portion in the vaporous state and cause the sample portion to condense into liquid format for delivery directly to a selected one of the receiving wells;
   a pick up station having a holding member that releasably retains the expansion chamber in a selected position for engagement by the dispensing head; and
   a chamber delivery assembly sized to contain a plurality of expansion chambers and having a delivery member positioned to deliver the expansion chamber to the pick up station.

8. The fraction collector assembly of claim 7, wherein the delivery member delivers the expansion chamber to the pick up station in the selected position.

9. The fraction collector assembly of claim 7 wherein the expansion chamber delivery assembly includes a hopper containing the plurality of expansion chambers, the hopper having an aperture positioned to deliver expansion chambers to the delivery member.

10. The fraction collector assembly of claim 7 wherein the expansion chamber delivery assembly includes a hopper containing the plurality of expansion chambers, the hopper having a directional orientation indicator for orientation of the expansion chambers within the hopper.

11. The fraction collector assembly of claim 7 wherein the expansion chamber delivery assembly includes a housing and a hopper removably retained in the, the hopper containing the plurality of expansion chambers, the hopper with the expansion chambers therein being insertable into and removeable from the housing as a unit.

12. The fraction collector assembly of claim 7, wherein the chamber delivery assembly having a chamber storage portion containing the plurality of expansion chambers, a dispensing drum rotatably mounted adjacent to the chamber storage portion and positioned to receive expansion chambers from the chamber storage portion, and an engagement member movably positioned to engage an expansion chamber on the dispensing drum and direct the expansion chamber toward the pick up station.

13. The fraction collector assembly of claim 12 further comprising a linear actuator connected to the engagement member and positioned to move the engagement member linearly relative to the dispensing drum.

14. The fraction collector assembly of claim 12 wherein the dispenser drum has a plurality of channels formed therein that receive the expansion chambers therein, the drum guide is positioned adjacent to the drum to retain the expansion chambers in selected channels as the dispenser drum rotates relative to the chamber storage portion.

15. The fraction collector assembly of claim 14 wherein the holding member of the pick up station is a first holding member, and the pick up station having a second holding member, the engagement member of the chamber delivery assembly is a first engagement member, the chamber delivery member having a second engagement member, the first and second engagement members being movable to independently direct two engagement members toward the first and second holding members, respectively.

16. The fraction collector assembly of claim 14 wherein the holding member of the pick up station is a first holding member, and the pick up station having a second holding member, the engagement member of the chamber delivery assembly is a first engagement member, the chamber delivery member having a second engagement member, the first and second engagement members being movable to direct two engagement members simultaneously toward the first and second holding members, respectively.

17. The fraction collector assembly of claim 7 wherein the delivery member of the chamber delivery assembly includes a slide portion movable relative to the holding member of the pick up station, the slide portion being positioned to receive the expansion chamber and to allow the expansion chamber to slide along the slide portion along a trajectory to the pick up stations holding member.

18. An automated fraction collector assembly useable to collect sample portions of a selected sample, comprising:
 a frame;
 a dispensing head movably connected to the frame, the dispensing head having a dispensing tube that receives the sample portion and dispense the sample portion, the dispensing head being movable between a dispensing position and a rinse position;
 a receiving container with a receiving well positioned to receive the sample portion of the selected sample dispensed from the dispensing tube when the dispensing head is in the dispensing position; and
 a rinse station connected to the frame and positioned to removably receive the dispensing tube when the dispensing head is in the rinse position.

19. The fraction collector assembly of claim 18 wherein the wash station includes a wash tube with an open end, the wash tube being sized to removably receive the dispensing tube therein through the open end, the wash tube being configured to contain a wash solution that engages the dispensing tube and washes the dispensing tube.

20. The fraction collector assembly of claim 19 wherein the dispensing tube is a dispensing needle.

21. The fraction collector assembly of claim 18 wherein the rinse station includes a rinse tube sized to receive a portion of the dispensing tube.

22. A fraction collector assembly useable to collect portions of a selected sample, comprising:
 a frame;
 a dispensing head movably connected to the frame, the dispensing head having at least one dispensing tube configured to dispense the portion of the selected sample, the dispensing head being movable between a pickup position, a wash position, and a dispensing position;
 a pickup station configured to releasably retain a selected chamber in a position for engagement by the dispensing head when in the pickup position;
 a wash station positioned to removably receive the dispensing tube when the dispensing head is in the wash position; and
 a docking station configured to retain a receiving container that receives the portion of the selected sample when the dispensing head is in the dispensing position.

23. The fraction collector assembly of claim 22, further comprising a storage container that contain the selected chambers before the selected chambers are positioned in the pickup station.

24. A fraction collector assembly useable to collect a purified portion of a selected sample taken from one of a plurality of supplying wells in a supplying container, the one supplying well having a well-position address for its position in the supplying container, comprising:
 a frame;
 a dispensing head movable relative to the frame along three axes of movement, the dispensing head being configured to dispense the portion of the selected sample, the dispensing head having a dispensing tube that receives the sample portion and dispense the sample portion, the dispensing head being movable between a dispensing position and a rinse position, the sample portion being provided to the dispensing head in a substantially vaporous state;
 a receiving container having a plurality of receiving wells sized to receive the sample portion of the selected sample when the dispensing head is in the dispensing position, each receiving well having a well-position address;
 an expansion chamber engageable by the dispensing head and being shaped to receive the sample portion from the in the vaporous state and cause the sample portion to condense into liquid format for delivery directly to a selected one of the receiving wells;
 a pick up station having a holding member that releasably retains the expansion chamber in a selected position for engagement by the dispensing head;
 a chamber delivery assembly sized to contain a plurality of expansion chambers and having a delivery member positioned to deliver the expansion chamber to the pick up station;
 a docking station releasably retaining the receiving container in a selected position to receive the sample portion;
 a computer controller configured to identify the well-position address for the one supplying well relative to the supplying container, the computer controller being coupled to the dispensing head and configured to control movement of the dispensing head relative to the docking station to dispense the sample portion directly into a receiving well having a well-position address relative to its position in the receiving container that directly corresponds to the well-position address of the one supplying well relative to the supplying container; and a rinse station connected to the frame and positioned to removably receive the dispensing tube when the dispensing head is in the rinse position.

25. The fraction collector assembly of claim 24 wherein the docking station has an indicator coupled to the computer controller, the indicator is positioned to identify where to position the receiving container in the docking station.

26. The fraction collector assembly of claim 24 wherein the expansion chamber delivery assembly includes a hopper containing the plurality of expansion chambers, the hopper having an aperture positioned to deliver expansion chambers to the delivery member.

27. The fraction collector assembly of claim 24 wherein the expansions chamber delivery assembly includes a housing and a hopper removably retained in the hopper containing the plurality of expansion chambers, the hopper with the expansion chambers therein being insertable into and removeable from the housing as a unit.

28. The fraction collector assembly of claim 24 wherein the chamber delivery assembly having a chamber storage portion containing the plurality of expansion chambers, a dispensing drum rotatably mounted adjacent to the chamber storage portion and positioned to receive expansion chambers from the chamber storage portion, and an engagement member movably positioned to engage an expansion chamber on the dispensing drum and direct the expansion chamber toward the pick up station.

29. The fraction collector assembly of claim 28 further comprising a linear actuator connected to the engagement member and positioned to move the engagement member linearly relative to the dispensing drum.

30. The fraction collector assembly of claim 28 wherein the dispenser drum has a plurality of channels formed therein that receive the expansion chambers therein, the drum guide is positioned adjacent to the drum to retain the expansion chambers in selected channels as the dispenser drum rotates relative to the chamber storage portion.

31. The fraction collector assembly of claim 24 wherein the holding member of the pick up station is a first holding member, and the pick up station having a second holding member, the engagement member of the chamber delivery assembly is a first engagement member, the chamber delivery member having a second engagement member, the first and second engagement members being movable to direct two engagement members simultaneously toward the first and second holding members, respectively.

32. The fraction collector assembly of claim 24 wherein the rinse station includes a sash tube with an open end, the wash tube being sized to removably receive the dispensing tube therein through the open end, the wash tube being configured to contain a wash solution that engages the dispensing tube and washes the dispensing tube.

33. The fraction collector assembly of claim 24 wherein the dispensing tube is a dispensing needle.

* * * * *

UNITED STATES PATENT AND TRADEMARK OFFICE
CERTIFICATE OF CORRECTION

PATENT NO. : 6,355,164
DATED : March 12, 2002
INVENTOR(S) : Wendell et al.

It is certified that error appears in the above-identified patent and that said Letters Patent is hereby corrected as shown below:

Column 3,
Line 7, "wells" should be -- well --;

Column 4,
Line 3, delete comma after "substantially";
Line 29, insert -- the -- between "in" and "second";

Column 6,
Line 34, "action" should be -- fraction --;

Column 12,
Line 49, "trough" should be -- through --;

Column 13,
Line 37, "circuits" should be -- circuit --;

Column 14,
Line 57, delete comma between "having" and "hardness";

Column 15,
Line 13, "thread" should be -- threads --;
Line 41, delete "b" between "approximately" and 0.0373";

Column 18,
Line 67, "tote" should be -- the --;

Column 22,
Line 19, delete comma after "2008";
Line 19, add comma between "embodiment" and "the";

Column 25,
Line 33, "sprig" should be -- spring --;

Column 26,
Line 2, delete colon between "the" and "dispensing";

UNITED STATES PATENT AND TRADEMARK OFFICE
CERTIFICATE OF CORRECTION

PATENT NO. : 6,355,164
DATED : March 12, 2002
INVENTOR(S) : Wendell et al.

It is certified that error appears in the above-identified patent and that said Letters Patent is hereby corrected as shown below:

Column 29,
Line 30, "embodiment" should be -- embodiments --;

Column 33,
Line 17, "expansions" should be -- expansion --;

Column 34,
Line 22, "sash" should be -- wash --;.

Signed and Sealed this

Twenty-first Day of May, 2002

Attest:

*Attesting Officer*

JAMES E. ROGAN
*Director of the United States Patent and Trademark Office*